(12) United States Patent
Suzuki et al.

(10) Patent No.: US 6,514,684 B2
(45) Date of Patent: Feb. 4, 2003

(54) BISPHENOL-PHOSPHOROUS COMPOUND COMPLEX AND THERMALLY PROCESSED IMAGE RECORDING MATERIAL UTILIZING THE SAME

(75) Inventors: Makoto Suzuki, Minami-ashigara (JP); Yasuhiro Yoshioka, Minami-ashigara (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 0 days.

(21) Appl. No.: 09/757,647

(22) Filed: Jan. 11, 2001

(65) Prior Publication Data

US 2002/0009683 A1 Jan. 24, 2002

(30) Foreign Application Priority Data

Jan. 11, 2000 (JP) ........................................ 2000-002428

(51) Int. Cl.$^7$ .............................................. G03C 1/498
(52) U.S. Cl. ........................ 430/617; 430/604; 430/610; 430/619
(58) Field of Search ................................ 430/619, 610, 430/617, 604

(56) References Cited

U.S. PATENT DOCUMENTS 6,174,663 B1 * 1/2001 Kato ........................... 430/619

FOREIGN PATENT DOCUMENTS

| EP | 0803764 A1 | 10/1997 |
|---|---|---|
| JP | 5151933 | 5/1976 |
| JP | 63793 | 1/1994 |

* cited by examiner

Primary Examiner—Thorl Chea
(74) Attorney, Agent, or Firm—Birch, Stewart, Kolasch & Birch, LLP

(57) ABSTRACT

Bisphenol-phosphorus compound complexes represented by the following general formula (1) are disclosed ($R^1$ to $R^4$ represent hydrogen atom or a group that can be a substituent on a benzene ring; L represents —S— group or a —$CHR^5$— group where $R^5$ represents hydrogen atom or an alkyl group; and $R^6$ to $R^8$ represent an alkyl group, an aryl group, a heterocyclic group etc.). The present invention provides reducing agents that can realize thermally processed image recording materials that can provide sufficient image density at a practical reaction temperature (specifically 100–140° C.) and within a practical reaction time (specifically 1–30 seconds), and can sufficiently suppress the coloration of white portions when the materials are stored in a dark place after the development.

7 Claims, 2 Drawing Sheets

R=0.048

X 31
Y 96
Z 61

BISPHENOL-PHOSPHOROUS COMPOUND COMPLEX AND THERMALLY PROCESSED IMAGE RECORDING MATERIAL UTILIZING THE SAME

FIELD OF THE INVENTION

The present invention relates to a bisphenol-phosphorus compound complex and a thermally processed image recording material containing it.

BACKGROUND OF THE INVENTION

As thermally processed image recording materials, there are a photothermographic material that has a photosensitive layer comprising a catalytically active amount of photocatalyst (e.g., silver halides), a heat developing agent, a reducible silver salt (e.g., silver salts of an organic acid), and a toning agent for controlling silver color tone as required, which are dispersed in a binder matrix, and a thermally processed image forming material that has a photosensitive layer comprising a heat developing agent, a reducible silver salt (e.g., silver salts of an organic acid), and a toning agent for controlling silver color tone as required, which are dispersed in a binder matrix. The thermally processed image forming material is heated imagewise at a high temperature to form monochromatic silver images through an oxidation-reduction reaction between the reducible silver salt (which functions as an oxidizing agent) and the heat developing agent. The photothermographic material is heated at a high temperature after imagewise light exposure to form monochromatic silver images through an oxidation-reduction reaction between the silver halide or the reducible silver salt (which functions as an oxidizing agent) and the heat developing agent. The oxidation-reduction reaction is accelerated by catalytic action of a latent image of silver halide generated upon exposure. Therefore, the monochromatic silver images are formed in exposed areas of the material. These materials are disclosed in many references including U.S. Pat. No. 2,910,377 and Japanese Patent Publication (Kokoku, hereinafter referred to as JP-B) 43-4924.

Since the aforementioned thermally processed image recording materials are not subjected to a fixation treatment after the heat development, they suffer from a problem that the thermally reactive silver salt of an organic acid and reducing agent are left as they are in the thermally processed image recording materials, and thus white portions are colored when the materials are stored for a long period of time after the development. o-Bisphenol type reducing agents are frequently used for the thermally processed image recording materials, since they show high reactivity. If their amounts are reduced, the coloration of white portions can be effectively suppressed. However, if the amounts of the o-bisphenol type reducing agents are reduced, sufficient image density can no longer be obtained. Therefore, it is difficult to compromise the image storability and the image density.

SUMMARY OF THE INVENTION

Therefore, an object of the present invention is to provide a thermally processed image recording material that can provide sufficient image density at a practical reaction temperature (specifically 100–140° C.) and within a practical reaction time (specifically 1–30 seconds), and can sufficiently suppress the coloration of white portions when the material is stored in a dark place after the development. Further, another object of the present invention is to provide a compound useful as a reducing agent that can reconcile the image density and the image storability.

The inventors of the present invention assiduously studied in order to achieve the aforementioned objects. As a result, they found a surprising effect that if a complex obtained from a bisphenol compound, which is known as a reducing agent used for thermally processed image recording materials (see, for example, European Patent Publication EP0803764A1, Japanese Patent Laid-open Publication (Kokai, hereinafter referred to as JP-A) 51-51933, JP-A-6-3793 etc.), and a phosphorus compound is used, sufficient image density could be obtained and the image storability was markedly improved without substantially decreasing the reducing property. Thus, the present invention was accomplished.

That is, the present invention provides bisphenol-phosphorus compound complexes represented by the following general formula (1):

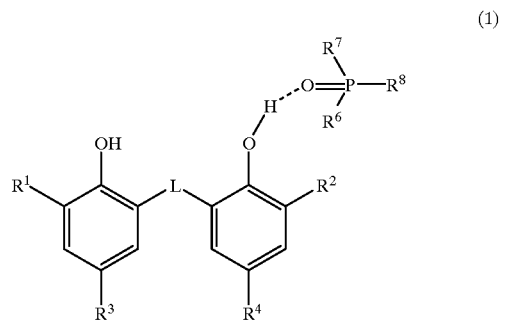

(1)

In the general formula (1) $R^1$, $R^2$, $R^3$ and $R^4$ each independently represent hydrogen atom or a group that can be a substituent on a benzene ring, and L represents —S— group or a —$CHR^5$— group. $R^5$ represents hydrogen atom or an alkyl group. $R^6$, $R^7$ and $R^8$ each independently represent an alkyl group, an aryl group, a heterocyclic group, —$N(R^9)(R^{10})$ or —$O(R^9)$. $R^9$ and $R^{10}$ each independently represent an alkyl group, an aryl group or a heterocyclic group. Two or more groups selected from $R^6$, $R^7$, $R^8$, $R^9$ and $R^{10}$ may be bound together to form a ring.

Preferred bisphenol-phosphorus compound complexes of the aforementioned general formula (1) are those wherein $R^1$, $R^2$, $R^3$ and $R^4$ each independently represent an alkyl group, L represents a —$CHR^5$— group, $R^5$ represents hydrogen atom or an alkyl group, $R^6$, $R^7$ and $R^8$ each independently represent an alkyl group, an aryl group or —$O(R^9)$, and $R^9$ represents an alkyl group or an aryl group.

The present invention also provides a thermally processed image recording material comprising a non-photosensitive silver salt of an organic acid, a reducing agent for silver ions and a binder on one surface of a support, wherein the thermally processed image recording material comprises at least one kind of the bisphenol-phosphorus compound complex represented by the aforementioned general formula (I).

The thermally processed image recording material of the present invention preferably contains at least one kind of photosensitive silver halide.

The thermally processed image recording material of the present invention utilizing the bisphenol-phosphorus compound complex represented by the following general formula (1) can provide sufficient image density at a practical reaction temperature (specifically 100–140° C.) and within a practical reaction time (specifically 1–30 seconds), and can sufficiently suppress the coloration of white portions when the material is stored in a dark place after the development.

PREFERRED EMBODIMENTS OF THE INVENTION

Figure 1:
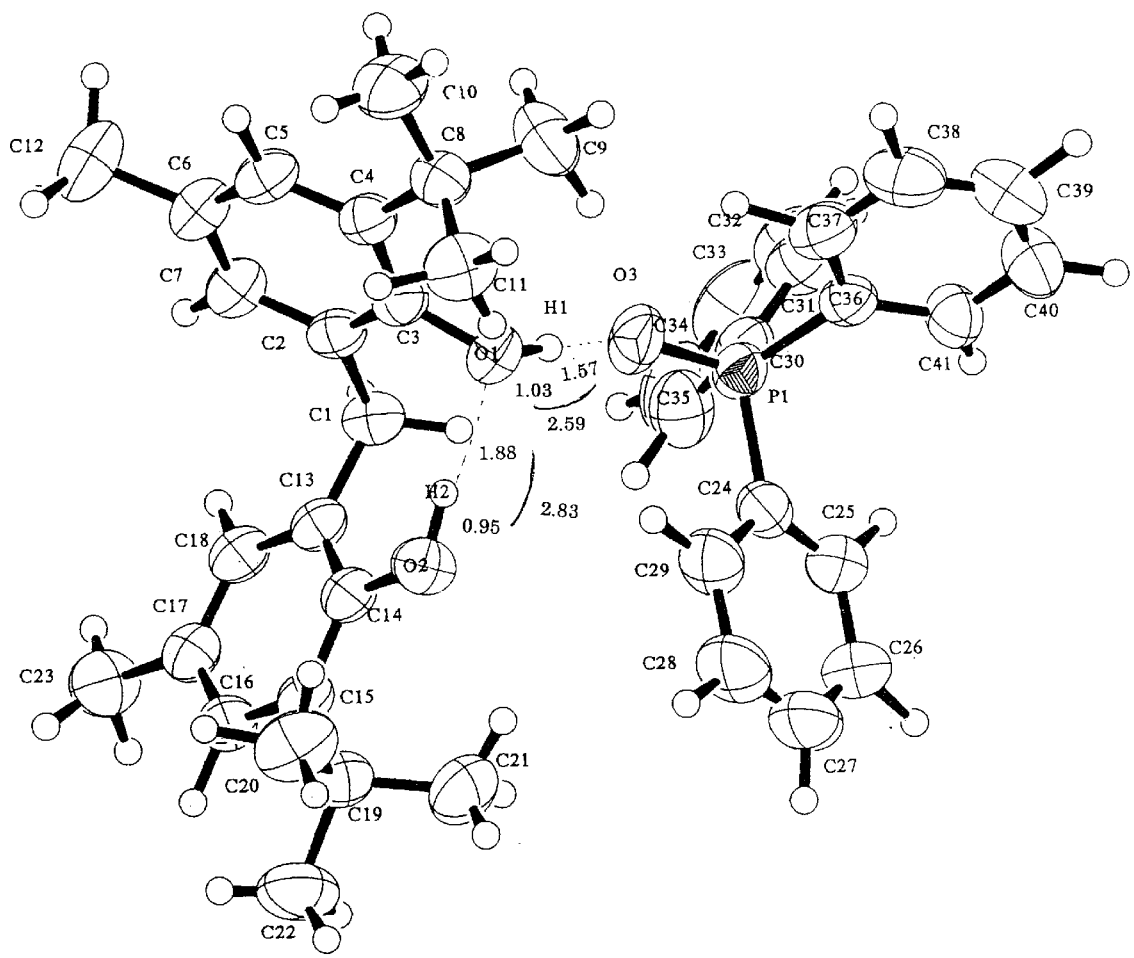
FIG. 1 shows the result of X-ray crystal diffraction analysis of Exemplary Compound 4 performed by using a tetraxial X-ray crystal diffraction measurement apparatus.
Figure 1:
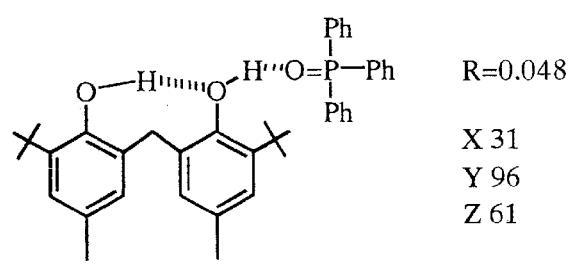

The bisphenol-phosphorus compound complex and the thermally processed image recording material of the present invention will be explained in detail hereinafter.

First, the bisphenol-phosphorus compound complex of the present invention represented by the general formula (I) will be explained in detail.

In the general formula (I), $R^1$ to $R^4$ represent hydrogen atom or a substituent that can be a substituent on a benzene ring, and they may be identical or different from one another. Examples of the substituent that can be a substituent on a benzene ring include a halogen atom (e.g., bromine atom, chlorine atom), an alkyl group having 1–15 carbon atoms, an aryl group having 6–26 carbon atoms (e.g., phenyl group, naphthyl group), an alkoxy group having 1–6 carbon atoms (e.g., methoxy group, ethoxy group, propyloxy group), an acylamino group having 2–7 carbon atoms (e.g., acetylamino group), a sulfonamido group having 1–6 carbon atoms (e.g., methanesulfonamido group), an acyl group having 2–7 carbon atoms (e.g., acetyl group), a carbamoyl group having 1–7 carbon atoms (e.g., carbamoyl group, dimethylcarbamoyl group), a sulfamoyl group having 0–6 carbon atoms (e.g., sulfamoyl group, dimethylsulfamoyl group), an alkoxycarbonyl group having 2–7 carbon atoms (e.g., methoxycarbonyl group, ethoxycarbonyl group), a sulfonyl group having 1–6 carbon atoms (e.g., methanesulfonyl group) and so forth. In the present specification, a numerical range represented with "-" includes values mentioned before and after it as the minimum value and maximum value.

$R^1$ and $R^2$ preferably represent an alkyl group, more preferably an alkyl group having 1–10 carbon atoms, and specific examples thereof include methyl group, ethyl group, propyl group, butyl group, isopropyl group, t-butyl group, t-amyl group, cyclohexyl group, 1-methylcyclohexyl group and so forth. Among these, methyl group, isopropyl group and t-butyl group are particularly preferred.

$R^3$ and $R^4$ preferably represent an alkyl group, more preferably an alkyl group having 1–10 carbon atoms, and specific examples thereof include methyl group, ethyl group, propyl group, butyl group, isopropyl group, t-butyl group, t-amyl group, cyclohexyl group, 1-methylcyclohexyl group, benzyl group and so forth. Among these, methyl group, ethyl group, isopropyl group and t-butyl group are more preferred, and methyl group and ethyl group are the most preferred.

L represents —S— group or a —CHR$^5$— group.

$R^5$ represents hydrogen atom or an alkyl group, preferably hydrogen atom or an alkyl group having 1–10 carbon atoms. Specific example of the alkyl group include methyl group, ethyl group, propyl group, butyl group, heptyl group, octyl group, undecyl group, isopropyl group, 1-ethylpentyl group, 2,4,4-trimethylpentyl group and so forth. $R^5$ is preferably hydrogen atom, methyl group, propyl group, isopropyl group or 2,4,4-trimethylpentyl group.

$R^6$, $R^7$ and $R^8$ each independently represent an alkyl group, an aryl group, a heterocyclic group, —N($R^9$)($R^{10}$) or —O($R^9$). $R^9$ and $R^{10}$ each independently represent an alkyl group, an aryl group or a heterocyclic group. Specific examples of the alkyl group include methyl group, ethyl group, propyl group, isopropyl group, butyl group, t-butyl group, t-amyl group, n-octyl group, cyclohexyl group, 1-methylcyclohexyl group, benzyl group and so forth. Specific examples of the aryl group include phenyl group, p-tolulyl group, m-tolulyl group, p-methoxyphenyl group, p-t-butylphenyl group and so forth. Specific examples of the heterocyclic group include 2-tetrahydrofuranyl group and pyridyl group.

Two or more groups selected from $R^6$, $R^7$, $R^8$, $R^9$ and $R^{10}$ may be bonded to each other or one another to form a ring. Specifically, $R^6$ and $R^7$, $R^7$ and $R^8$, $R^6$ and $R^8$, $R^6$ and $R^9$, $R^7$ and $R^9$, $R^7$ and $R^{10}$, and $R^9$ and $R^{10}$ each may be bonded to form a ring. Specifically, the exemplary compounds (29) and (30) shown below can be referred to.

Particularly preferred compounds represented by the general formula (1) are those wherein $R^1$, $R^2$, $R^3$ and $R^4$ each independently represent an alkyl groups, L represents a —CHR$^5$— group, R represents hydrogen atom or an alkyl group, $R^6$, $R^7$ and $R^8$ each independently represent an alkyl group, an aryl group or —O($R^9$), and $R^9$ represents an alkyl group or an aryl group.

Specific examples of the bisphenol-phosphorus compound complex represented by the general formula (1) will be listed below. However, the compound of the present invention is not limited to these specific examples.

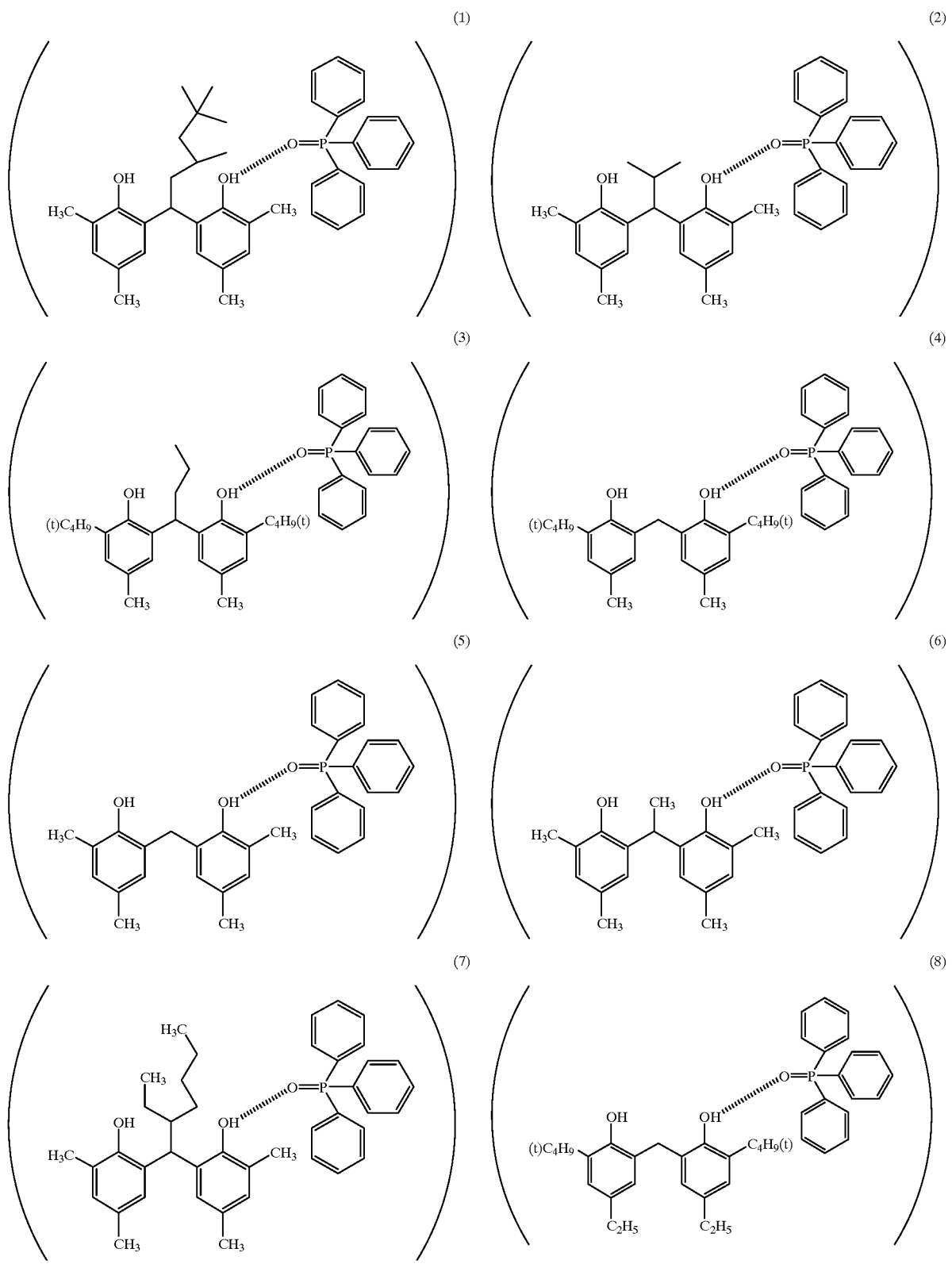

-continued
(9)
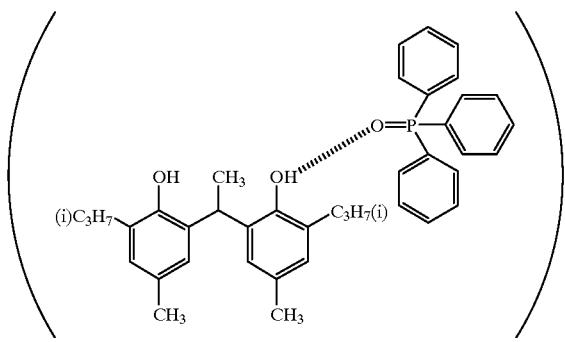
(10)
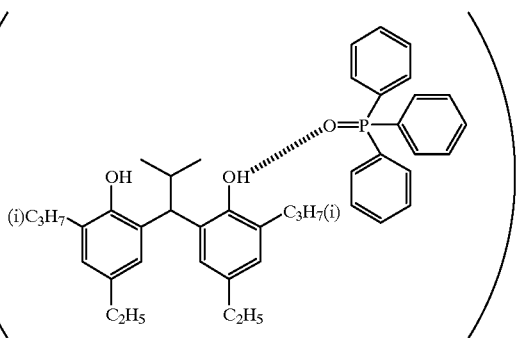
(11)
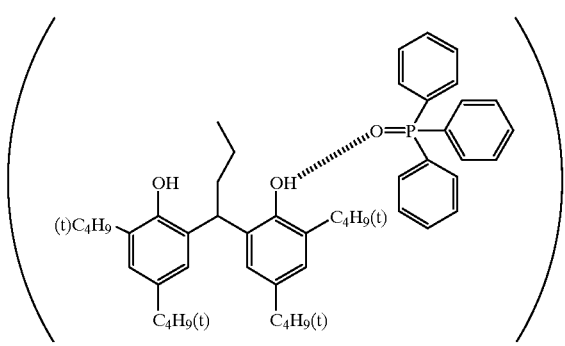
(12)
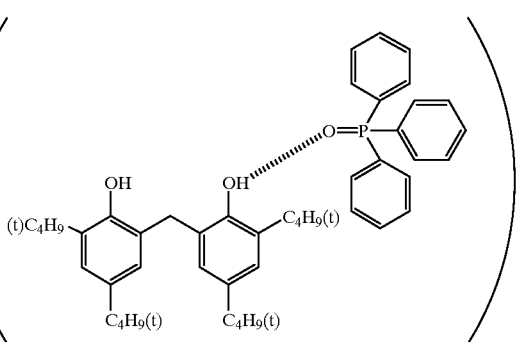
(13)
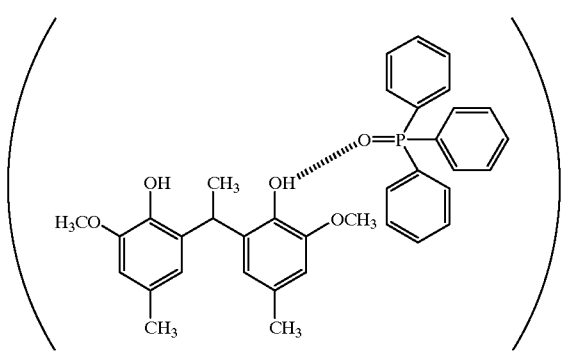
(14)
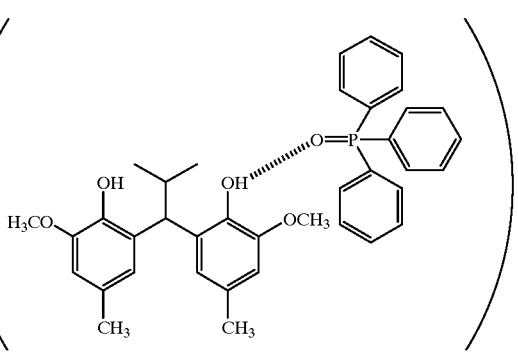
(15)
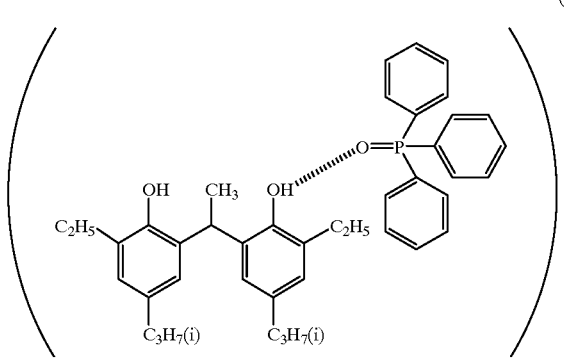
(16)
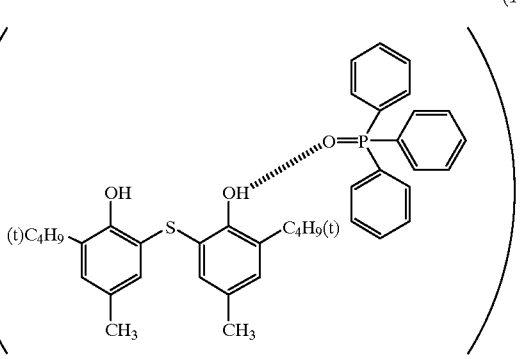

-continued
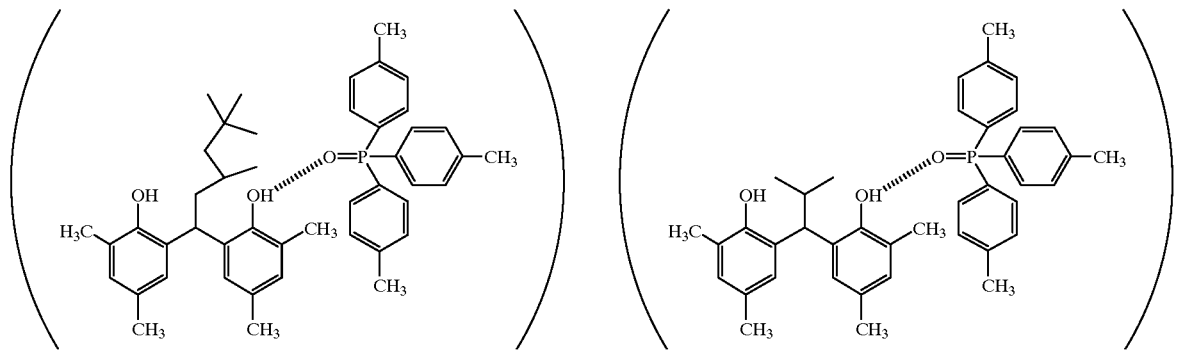
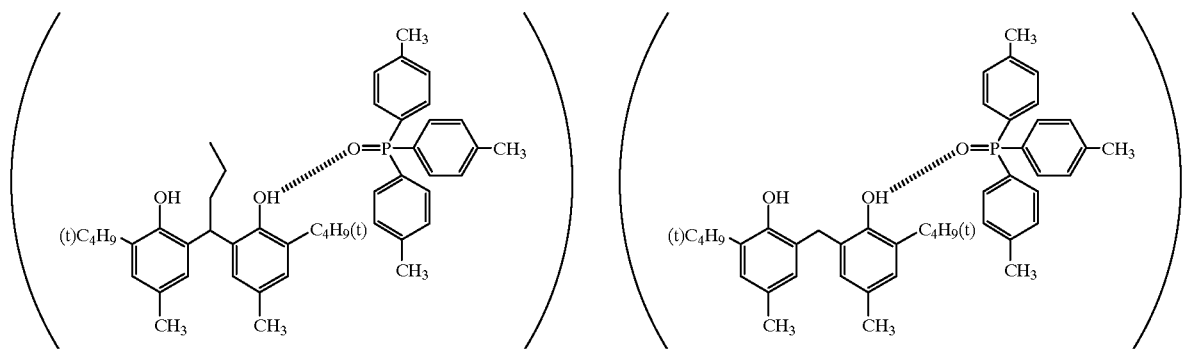
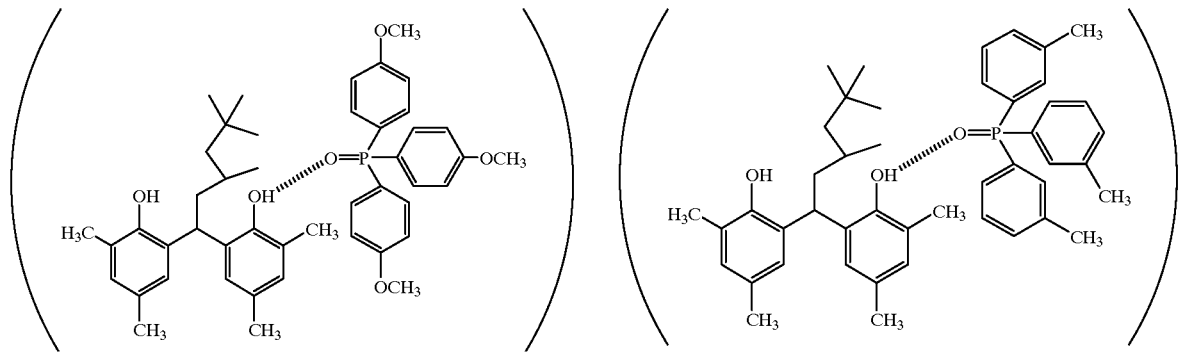
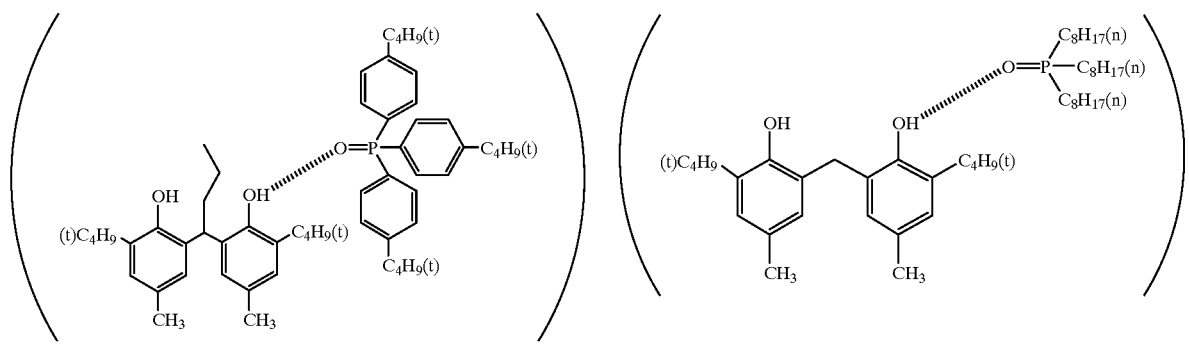

-continued
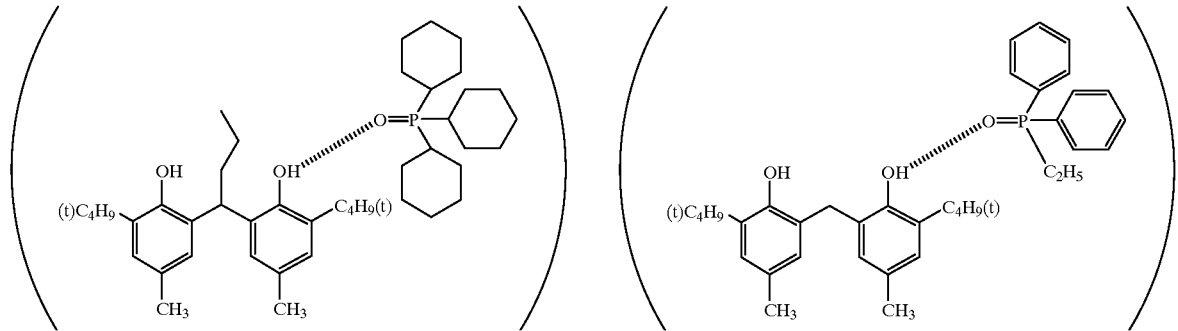
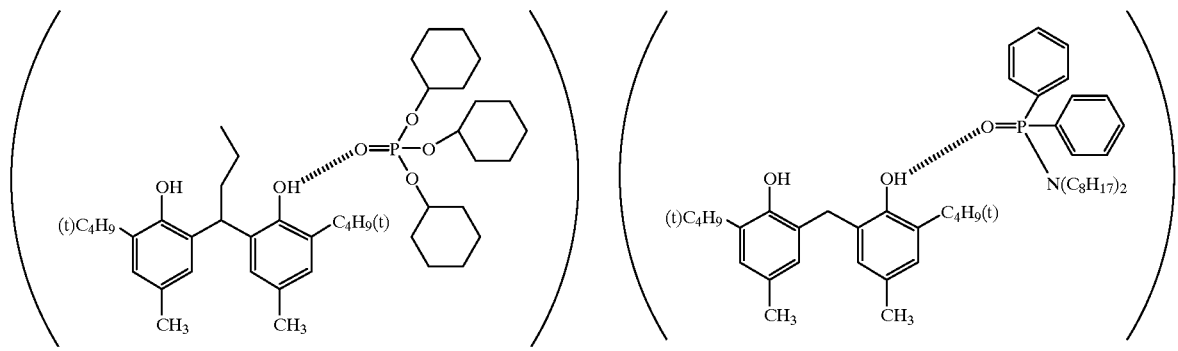
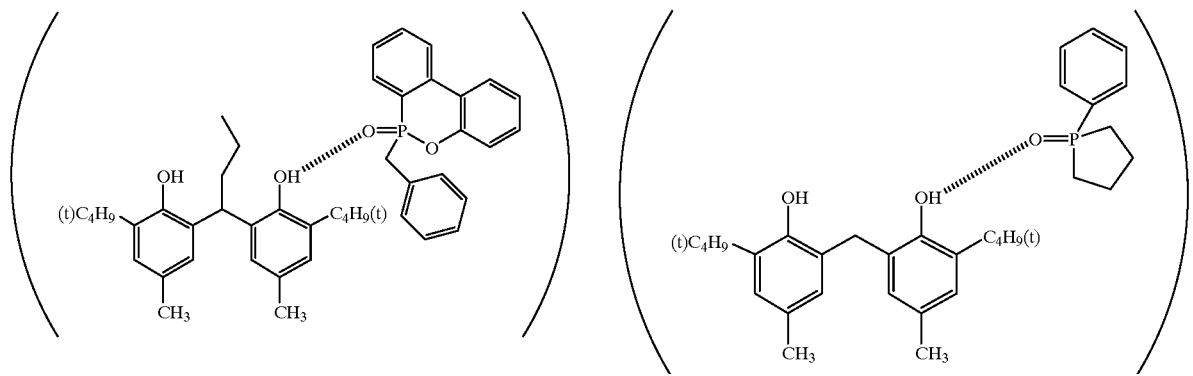
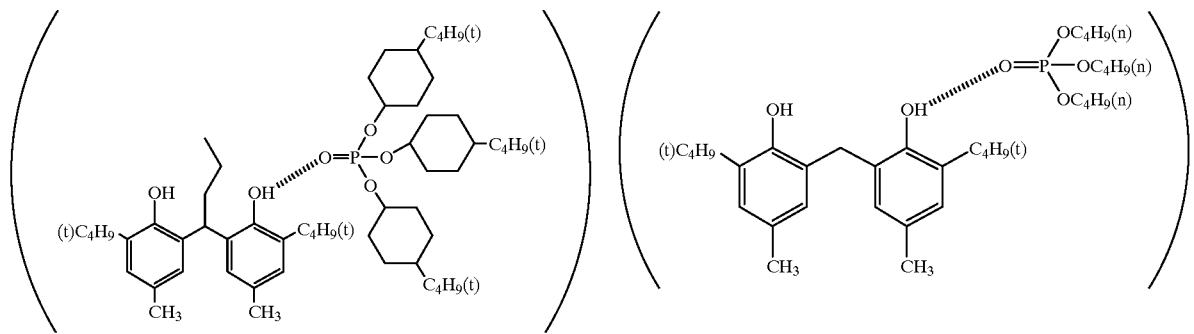

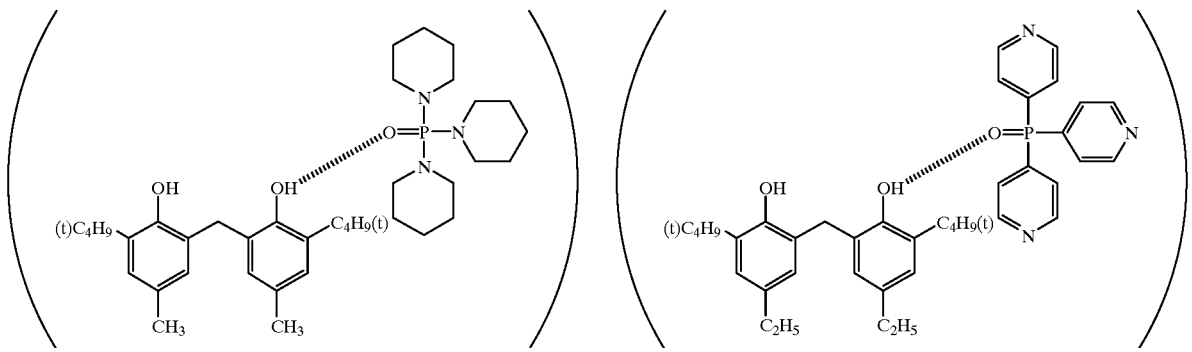

The method for producing the bisphenol-phosphorus compound complex represented by the general formula (1) is not particularly limited. For example, it can be prepared by dissolving 1 mole of an o-bisphenol and 0.7–1.3 moles of a phosphorus compound in an organic solvent. If necessary, they may be dissolved with heating. As the organic solvent, ethyl acetate, hexane, toluene, acetone, acetonitrile and alcohols having 4 or less carbon atoms are preferred, and ethyl acetate, acetone and acetonitrile are more preferred. The amount of the organic solvent used can be arbitrarily selected within the range of 1 to 50 times, preferably 2 to 15 times, as much as the o-bisphenol in terms of weight ratio. The complex can be obtained by leaving the solution as it is. However, when the amount of the solvent is large, the complex can be obtained by evaporating a part of the solvent under reduced pressure or atmospheric pressure and leaving the solution, or by adding hexane or water to the solution with cooling. As a combination of solvents, ethyl acetate/hexane, acetone/water and acetonitrile/water are preferred.

If the bisphenol-phosphorus compound complex represented by the general formula (1) is used as a reducing agent in a thermally processed image recording material, sufficient image density can be obtained at a practical reaction temperature (specifically 100–140° C.) and within a practical reaction time (specifically 1–30 seconds), and the coloration of white portions can be sufficiently suppressed even when the material is stored in a dark place after the development, and thus it is extremely useful.

When the bisphenol-phosphorus compound complex represented by the general formula (1) is used for a thermally processed image recording material, the bisphenol-phosphorus compound complex is contained in an amount of preferably 5–50 mole %, more preferably 10–40 mole %, of silver on the side having the image-forming layer. The thermally processed image recording material may contain a reducing agent other than the bisphenol-phosphorus compound complex represented by the general formula (1) in combination. Reducing agents that can be combined will be mentioned later.

When the bisphenol-phosphorus compound complex represented by the general formula (1) is used in a thermally processed image recording material, the bisphenol-phosphorus compound complex may be added to a coating solution in any form such as solution, emulsion dispersion and solid microparticle dispersion to be incorporated in the thermally processed image recording material.

As a well known emulsion dispersion method, there can be mentioned a method of dissolving the compound in an oil such as dibutyl phthalate, tricresyl phosphate, glyceryl triacetate or diethyl phthalate by using an auxiliary solvent such as ethyl acetate or cyclohexanone and mechanically preparing an emulsion dispersion.

As the method for preparing solid microparticle dispersion, there can be mentioned a method of dispersing powder of the bisphenol-phosphorus compound complex represented by the general formula (1) in a suitable solvent such as water by using a ball mill, colloid mill, vibrating ball mill, sand mill, jet mill, roller mill or ultrasonic wave to form solid dispersion. In this operation, a protective colloid (e.g., polyvinyl alcohol), surfactant (e.g., an anionic surfactant such as sodium triisopropylnaphthalenesulfonate (mixture of those having three isopropyl groups on different positions)) and so forth may be used. An aqueous dispersion may contain a preservative (e.g., benzisothiazolinone sodium salt).

Now, thermally processed image recording materials in which the bisphenol-phosphorus compound complex represented by the general formual (1) can be used will be explained in detail hereinafter.

A thermally processed image recording material comprises at least a non-photosensitive silver salt of an organic acid, a reducing agent for silver ions and a binder on one surface of a support. The thermally processed image recording material referred to in the present specification include at least a thermally processed image forming material and a photothermographic material. The photothermographic material comprises at least a photosensitive silver halide, a non-photosensitive silver salt of an organic acid, a reducing agent for silver ions and a binder on one surface of a support.

A silver salt of an organic acid that can be used in the present invention is a silver salt relatively stable against light, but forms a silver image when it is heated at 80° C. or higher in the presence of an exposed photocatalyst (e.g., a latent image of photosensitive silver halide) and a reducing agent. The silver salt of an organic acid may be any organic substance containing a source capable of reducing silver ions. Such light insensitive silver salts of an organic acid are disclosed in JP-A-10-62899, paragraphs 0048 to 0049 and EP0803763A1, page 18, line 24 to page 19, line 37. Silver salts of an organic acid, in particular, silver salts of a long chained aliphatic carboxylic acid (having from 10 to 30, preferably from 15 to 28 carbon atoms) are preferred. Preferred examples of the silver salt of an organic acid include silver behenate, silver arachidinate, silver stearate, silver oleate, silver laurate, silver caproate, silver myristate, silver palmitate, mixtures thereof and so forth. In the present invention, a silver salt of an organic acid containing 75% or more of silver behenate is preferably used among these silver bahenate.

The shape of the silver salt of an organic acid that can be used for the present invention is not particularly limited. However, scaly silver salts of an organic acid are preferred for the present invention. A scaly silver salt of an organic acid are herein defined as follows. A sample of a silver salt of an organic acid to be analyzed is observed with an electronic microscope, and grain shapes of the salt seen in the field are approximated to rectangular parallelepipeds. The three different edges of each rectangular parallelepiped are represented as a, b and c where a is the shortest, c is the longest, and c and b may be the same. From the shorter edges a and b, x is obtained according to the following equation:

$$x=b/a$$

The values of x are obtained for about 200 grains seen in the field, and an average of them (x(average)) is obtained. Samples that satisfy the requirement of $x(average) \geq 1.5$ are defined to be scaly. Scaly grains preferably satisfy $30 \geq x(average) \geq 1.5$, more preferably $20 \geq x(average) \geq 2.0$. In this connection, acicular (needle-like) grains satisfy $1 \leq x(average) < 1.5$.

In scaly grains, it is understood that a corresponds to the thickness of tabular grains of which main planes are defined by the sides of b and c. The average of a is preferably from 0.01 μm to 0.23 μm, more preferably from 0.1 μm to 0.20 μm. The average of c/b is preferably from 1 to 6, more preferably from 1.05 to 4, even more preferably from 1.1 to 3, particularly preferably from 1.1 to 2.

The grain size distribution of the silver salt of an organic acid is preferably monodispersed. The term "monodispersed" as used herein means that the percentage of the value obtained by dividing the standard deviation of the length of the short axis or long axis by the length of the short axis or long axis, respectively, is preferably 100% or less, more preferably 80% or less, further preferably 50% or less. The shape of the silver salt of an organic acid can be determined from a transmission electron microscope image of organic acid silver salt dispersion. Another method for determining the monodispesibility is a method of obtaining the standard deviation of a volume weight average diameter of the silver salt of an organic acid. The percentage (coefficient of variation) of the value obtained by dividing the standard deviation by the volume weight average diameter of the silver salt of an organic acid is preferably 100% or less, more preferably 80% or less, further preferably 50% or less. As a measurement method, for example, the grain size (volume weight average diameter) can be determined by irradiating organic acid silver salt dispersed in a solution with a laser ray and determining an autocorrelation function of the fluctuation of the scattered light on the basis of the change in time.

For the preparation of the silver salt of an organic acid and as dispersion method therefor, known methods can be used. For example, the aforementioned JP-A-10-62899, EP0803763A1 and European Patent Application 99110902.6 can be referred to.

It is desirable that the silver salt of an organic acid is dispersed substantially in the absence of a photosensitive silver salt, since the photosensitive silver salt will increase fog and markedly lower sensitivity, if it is present during the dispersion. In the present invention, the amount of the photosensitive silver salt that may be in the aqueous dispersion of the silver salt of an organic acid should be 0.1 mole % or less per mole of the silver salt of an organic acid, and the photosensitive silver salt is not added intentionally.

In the present invention, the thermally processed image recording material can be produced by mixing an aqueous dispersion of the silver salt of an organic acid and an aqueous dispersion of the photosensitive silver salt. While the mixing ratio of the silver salt of an organic acid and the photosensitive silver salt can be selected depending on the purpose, the ratio of the photosensitive silver salt with respect to the silver salt of an organic acid is preferably in the range of 1–30 mole %, more preferably 3–20 mole %, particularly preferably 5–15 mole %. For the mixing of them, mixing two or more kinds of aqueous dispersions of the silver salt of an organic acid and two or more kinds of aqueous dispersions of the photosensitive silver salt is preferably used for controlling photographic properties.

While the silver salt of an organic acid can be used in a desired amount, it is preferably used in an amount of 0.1–5 g/m², more preferably 1–3 g/m², as the amount of silver.

The thermally processed image recording material of the present invention contains a reducing agent for silver ions. The reducing agent for silver ions may be any substance (preferably an organic substance) capable of reducing silver ions into metal silver. Some examples of the reducing agent are described in JP-A-11-65021, paragraphs 0043 to 0045 and EP 0803764A1, from page 7, line 34 to page 18, line 12. Especially preferred for use in the present invention are bisphenol-type reducing agents (e.g., 1,1-bis(2-hydroxy-3, 5-dimethylphenyl)-3,5,5-trimethylhexane, 2,2'-methylenebis-(4-methyl-6-tert-butylphenol), 2,2'-methylenebis-(4-ethyl-6-tert-butylphenol)). The amount of the reducing agent is preferably from 0.01–5.0 g/m², more preferably from 0.1–3.0 g/m². The amount of the reducing agent is preferably 5–50 mole %, more preferably 10–40 mole %, per mole of silver on the image-forming layer side. The reducing agent is preferably contained in the image-forming layer.

The reducing agent may be added to a coating solution in any form such as solution, emulsion dispersion and solid microparticle dispersion to be incorporated in the thermally processed image recording material.

As a well known emulsion dispersion method, there can be mentioned a method of dissolving the compound in an oil such as dibutyl phthalate, tricresyl phosphate, glyceryl triacetate or diethyl phthalate by using an auxiliary solvent such as ethyl acetate or cyclohexanone and mechanically preparing an emulsion dispersion.

As the method for preparing solid microparticle dispersion, there can be mentioned a method of dispersing powder of the reducing agent in a suitable solvent such as water by using a ball mill, colloid mill, vibrating ball mill, sand mill, jet mill, roller mill or ultrasonic wave to form solid dispersion. In this operation, a protective colloid (e.g., polyvinyl alcohol), surfactant (e.g., an anionic surfactant such as sodium triisopropylnaphthalenesulfonate (mixture of those having three isopropyl groups on different positions)) and so forth may be used. An aqueous dispersion may contain a preservative (e.g., benzisothiazolinone sodium salt).

In the thermally processed image recording material of the present invention, the phenol derivatives represented by the formula (A) mentioned in Japanese Patent Application No. 11-73951 are preferably used as a development accelerator.

The photosensitive silver halide that can be used for the present invention is not particularly limited as for the halogen composition, and silver chloride, silver chlorobromide, silver bromide, silver iodobromide, and silver chloroiodobromide may be used. The halide composition may have a uniform distribution in the grains, or the compositions may change stepwise or continuously in the grains. Silver halide grains having a core/shell structure may be preferably used. Core/shell grains having preferably a double to quintuple structure, more preferably a double to quadruple structure may be used. A technique for localizing silver bromide on the surface of silver chloride or silver chlorobromide grains may also be preferably used.

For the preparation of the photosensitive silver halide, methods well known in the art, e.g., the methods described in Research Disclosure, No. 17029 (June, 1978) and U.S. Pat. No. 3,700,458, can be used. More specifically, a method can be used which comprises the step of preparing photosensitive silver halide grains by addition of a silver-supplying compound and a halogen-supplying compound to a solution of gelatin or other polymer, and then mixing the resulting grains with a silver salt of an organic acid. The methods disclosed in JP-A-119374, paragraphs 0217 to 0224, Japanese Patent Application Nos. 11-98708 and 11-84182 are also preferred.

As for a grain size of the photosensitive silver halide, smaller grains are desirable to prevent cloudiness of the photosensitive material after image formation. Specifically, the grain size may preferably be not greater than 0.20 $\mu$m, preferably 0.01–0.15 $\mu$m, more preferably 0.02–0.12 $\mu$m. The term "grain size" used herein means a diameter of a sphere having the same volume as the grain where the silver halide grains are regular crystals in cubic or octahedral form and where the silver halide grains are irregular crystals such as spherical or rod-like grains. Where silver halide grains are tabular grains, the term means the diameter of a circle having the same area as a projected area of the main surface of the tabular grain.

Examples of the form of silver halide grains include a cubic form, octahedral form, tabular form, spherical form, rod-like form and potato-like form. In particular, cubic grains are preferred for the present invention. Silver halide grains having round corners are also preferably used in the present invention. Surface index (Miller index) of outer surfaces of the photosensitive silver halide grains is not particularly limited. However, it is desirable that the [100] face should be present in a high proportion that can achieve high spectral sensitizing efficiency when a spectral sensitizing dye adsorbs on the grains. The proportion of the [100] face may be preferably not lower than 50%, more preferably at least 65%, still more preferably at least 80%. The proportion of Miller index [100] face can be determined using the method described in T. Tani, J. Imaging Sci., 29, 165 (1985), which utilizes the difference in adsorption of a sensitizing dye to [111] face and [100] face.

The photosensitive silver halide grain contains a metal or metal complex of Group VIII to Group X in the periodic table of elements (including Group I to Group XVIII). The metal or the center metal of the metal complex of Group VIII to X of the periodic table is preferably rhodium, ruthenium or iridium. The metal complex may be used alone, or two or more complexes of the same or different metals may also be used in combination. The metal complex content is preferably from $1\times10^{-9}$ to $1\times10^{-3}$ mole per mole of silver. Such heavy metals and metal complexes as well as addition method therefor are described in JP-A-7-225449, JP-A-11-65021, paragraphs 0018 to 0024, and JP-A-11-119374, paragraphs 0227 to 0240.

In the present invention, an iridium compound is preferably contained in the silver halide grains. Examples of the iridium compound include hexachloroiridium, hexammineiridium, trioxalatoiridium and hexacyanoiridium. The iridium compound is used after dissolving it in water or an appropriate solvent, and a method commonly used for stabilizing the iridium compound solution, more specifically, a method comprising adding an aqueous solution of hydrogen halide (e.g., hydrochloric acid, bromic acid, fluoric acid) or alkali halide (e.g., KCl, NaCl, KBr, NaBr etc.) may be used. In place of using a water-soluble iridium, separate silver halide grains previously doped with iridium may be added and dissolved at the time of preparation of silver halide. The addition amount of the iridium compound is preferably $1\times10^{-8}$ to $1\times10^{-3}$ mole, more preferably $1\times10^{-7}$ to $5\times10^{-4}$ mole, per mole of silver halide.

The silver halide emulsion used in the present invention may be added with a thiosulfonic acid compound according to the method disclosed in European Patent Publication No. 293,917.

Further, metal complexs that can be contained in the silver halide grains used for the present invention (e.g., [Fe $(CN)_6]^{4-}$), desalting methods and chemical sensitization methods are described in JP-A-11-84574, paragraphs 0046 to 0050, JP-A-11-65021, paragraphs 0025 to 0031, and JP-A-11-119374, paragraphs 0242 to 0250.

As gelatin contained in the photosensitive silver halide emulsion used for the present invention, various kinds of gelatin may be used. In order to obtain good dispersion state of the photosensitive silver halide emulsion in a coating solution containing a silver salt of an organic acid, low molecular weight gelatin having a molecular weight of 500–60,000 is preferably used. While such low molecular weight gelatin may be used during the grain formation or the dispersion operation after the desalting treatment, it is preferably used during the dispersion operation after the desalting treatment.

As a sensitizing dye that can be used for the present invention, there can be advantageously selected those sensitizing dyes which can spectrally sensitize silver halide grains within a desired wavelength range after they are adsorbed by the silver halide grains and have spectral sensitivity suitable for spectral characteristics of the light source to be used for exposure. Such sensitizing dyes and addition methods therefor are described in JP-A-11-65021, paragraphs 0103 to 0109, JP-A-10-18657 as for the compounds represented by the formula (II), JP-A-11-119347 as for the dyes represented by the formula (I) and paragraph 0106, U.S. Pat. Nos. 5,510,236, 3,871,887 as for the dyes disclosed in Example 5, JP-A-2-96131, JP-A-59-48753 as for the dyes disclosed therein and EP 0803764A1, page 19, line 38 to page 20, line 35. These dyes may be used each alone or in any combination of two or more of them. In the present invention, the sensitizing dye is added to the silver halide emulsion preferably during the period after the desalting step and before the coating step, more preferably during the period after the desalting step and before the start of the chemical ripening.

While the amount of the sensitizing dye used in the present invention may be selected to be a desired amount depending on the performance including sensitivity and fog, it is preferably $10^{-6}$ to 1 mole, more preferably $10^{-4}$ to $10^{-1}$ mole, per mole of silver halide in the photosensitive layer.

In the present invention, a supersensitizer can be used in order to improve spectral sensitization efficiency. Examples of the supersensitizer that can be used for the present invention include compounds disclosed in EP-A-587338, U.S. Pat. Nos. 3,877,943, 4,873,184, JP-A-5-341432, JP-A-11-109547, JP-A-10-111543 and so forth.

Photosensitive silver halide grains used for the present invention are preferably subjected to chemical sensitization by sulfur sensitization, selenium sensitization or tellurium sensitization. Any known compounds are preferably usable for such sulfur, selenium or tellurium sensitization, and for example, the compounds described in JP-A-7-128768 and so forth are usable for that purpose. In the present invention, tellurium sensitization is particularly preferred, and the compounds described in JP-A-11-65021, paragraph 0030 and the compounds of formulas (II), (III) and (IV) given in JP-A-5-313284 are more preferred.

In the present invention, the chemical sensitization may be performed at any time so long as it is performed after the formation of the grains and before the coating. It may be performed after desalting and (1) before the spectral sensitization, (2) simultaneously with the spectral sensitization, (3) after the spectral sensitization, (4) immediately before the coating, or the like. It is particularly preferably performed after spectral sensitization.

The amount of the sulfur, selenium or tellurium sensitizer for use in the present invention varies depending on the type of the silver halide grains to be used, the condition for chemical ripening etc., but may fall generally between $10^{-8}$ and $10^{-2}$ mole, preferably between $10^{-7}$ and $10^{-3}$ mole or so, per mol of the silver halide. Although the conditions for the chemical sensitization are not particularly limited in the present invention, in general, pH is in the range of 5–8, the pAg in the range of 6–11, and the temperature in the range of 40–95° C.

In the thermally processed image recording material of the present invention, one kind of photosensitive silver halide emulsion may be used or two or more different emulsions (for example, those having different average grain sizes, different halogen compositions, different crystal habits or different chemical sensitization conditions) may be used in combination. By using plural photosensitive silver halides having different sensitivities, contrast can be controlled. Examples of the techniques concerning this respect include those mentioned in JP-A-57-119341, JP-A-53-106125, JP-A-47-3929, JP-A-48-55730, JP-A-46-5187, JP-A-50-73627, JP-A-57-150841 and so forth. Each emulsion may preferably have sensitivity difference of 0.2 log E or higher.

The amount of the photosensitive silver halide is preferably 0.03 to 0.6 g/m$^2$, more preferably 0.05 to 0.4 g/m$^2$, most preferably 0.1 to 0.4 g/m$^2$, as the amount of coated silver per 1 m$^2$ of the thermally processed image recording material. The amount of the photosensitive silver halide per mole of the silver salt of an organic acid is preferably from 0.01 to 0.5 mole, more preferably from 0.02 to 0.3 mole.

Methods and conditions for mixing photosensitive silver halide and a silver salt of an organic acid, which are separately prepared, are not particularly limited so long as the effect of the present invention can be attained satisfactorily. Examples thereof include, for example, a method of mixing silver halide grains and a silver salt of an organic acid after completion of respective preparations by using a high-speed stirring machine, ball mill, sand mill, colloid mill, vibrating mill, homogenizer or the like, or a method of preparing a silver salt of an organic acid by mixing a photosensitive silver halide obtained separately at any time during the preparation of the silver salt of an organic acid. For the mixing of them, mixing two or more kinds of aqueous dispersions of the silver salt of an organic acid and two or more kinds of aqueous dispersions of the photosensitive silver salt is preferably used for controlling photographic properties.

Preferred addition time point for the silver halide into the coating solution for image-forming layer resides in a period of from 180 minutes before the coating to immediately before the coating, preferably 60 minutes to 10 seconds before the coating. However, the method and conditions for mixing are not particularly limited so long as the effect of the present invention can be attained satisfactorily. Specific examples of the mixing method include a method in which the mixing is performed in a tank designed so that a desired average residence time therein can be obtained, which residence time is calculated from addition flow rate and feeding amount to a coater, a method utilizing a static mixer described in N. Harnby, M. F. Edwards, A. W. Nienow, "Ekitai Kongo Gijutsu (Techniques for Mixing Liquids)", translated by Koji Takahashi, Chapter 8, Nikkan Kogyo Shinbunsha, 1989 and so forth.

In the present invention, improved performance can be obtained when the layer containing silver salt of an organic acid is formed by applying a coating solution comprising 30% by weight or more of water as to the total solvent in addition to organic solvent and drying it, more preferably when the binder of the image-forming layer is soluble or dispersible in an aqueous solvent (water solvent), in particular, it is a polymer latex showing an equilibrated moisture content of 2 weight % or less at 25° C. and relative humidity of 60%. In the most preferred embodiment, the polymer latex is prepared to have an ion conductivity of 2.5 mS/cm or less. As a method for preparing such polymer latex, there can be mentioned a method comprising synthesizing a polymer and purifying it by using a functional membrane for separation.

The aqueous solvent in which the polymer binder is soluble or dispersible used herein is water or a mixed solvent of water and 70% by weight or less of a water-miscible organic solvent. Examples of the water-miscible organic solvent include, for example, alcohols such as methyl alcohol, ethyl alcohol and propyl alcohol; cellosolves such as methyl cellosolve, ethyl cellosolve and butyl cellosolve; ethyl acetate, dimethylformamide and so forth.

The terminology "aqueous solvent" referred to herein is also used for systems in which the polymer is not thermodynamically dissolved but is present in a so-called dispersed state.

The "equilibrated moisture content at 25° C. and relative humidity of 60%" referred to herein for polymer latex is represented by the following equation, in which W1 indicates the weight of a polymer in humidity-conditioned equilibrium at 25° C. and relative humidity of 60%, and W0 indicates the absolute dry weight of the polymer at 25° C.

Equilibrated moisture content at 25° C. and relative humidity of 60%

$$=[(W1-W0)/W0]\times 100 \text{(weight \%)}$$

For the details of the definition of moisture content and the method for measuring it, for example, there can be referred Lecture of Polymer Engineering, 14, Test Methods for Polymer Materials (Polymer Society of Japan, Chijin Shokan).

The equilibrated moisture content at 25° C. and relative humidity of 60% of the binder polymer is preferably 2% by weight or less, more preferably from 0.01 to 1.5% by weight, even more preferably from 0.02 to 1% by weight.

In the present invention, polymers dispersible in aqueous solvents are particularly preferred. Examples of the dispersed state include, for example, that of polymer latex in which fine particles of water-insoluble hydrophobic polymer are dispersed, that in which a polymer is dispersed in a molecular state or as micelles and so forth, and all of them are preferred. Mean particle diameter of the dispersed particle is preferably in the range of about 1–50,000 nm, more preferably about 5–5,000 nm. The particle diameter distribution of the dispersed particles is not particularly limited, and either those having a wide particle diameter distribution or those having monodispersed particle diameter distribution may be used.

In a preferred embodiment of the present invention, hydrophobic polymers such as acrylic resins, polyester resins, rubber resins (e.g., SBR resins), polyurethane resins, polyvinyl chloride resins, polyvinyl acetate resins, polyvinylidene chloride resins and polyolefin resins can preferably be used. The polymers may be linear, branched or crosslinked. They may be so-called homopolymers in which a single kind of monomer is polymerized, or copolymers in which two or more different kinds of monomers are polymerized. The copolymers may be random copolymers or block copolymers. The polymers may have a number average molecular weight of 5,000 to 1,000,000, preferably from 10,000 to 200,000. Polymers having a too small molecular weight may suffer from insufficient mechanical strength of the emulsion layer, and those having a too large molecular weight may suffer from bad film forming property. Thus, they are not preferred.

Specific examples of the preferred polymer latex are mentioned below. They are expressed with the constituent monomers. The numerals parenthesized indicate the contents in terms of % by weight. The molecular weights are number average molecular weights.

P-1: Latex of -MMA(70)-EA(27)-MAA(3)-(molecular weight: 37000)

P-2: Latex of -MMA(70)-2EHA(20)-St(5)-AA(5)-(molecular weight: 40000)

P-3: Latex of -St(50)-Bu(47)-MMA(3)-(molecular weight: 45000)

P-4: Latex of -St(68)-Bu(29)-AA(3)-(molecular weight: 60000)

P-5: Latex of -St(70)-Bu(27)-IA(3)-(molecular weight: 120000)

P-6: Latex of -St(75)-Bu(24)-AA(1)-(molecular weight: 108000)

P-7: Latex of -St(60)-Bu(35)-DVB(3)-MAA(2)-(molecular weight: 150000)

P-8: Latex of -St(70)-Bu(25)-DVB(2)-AA(3)-(molecular weight: 280000)

P-9: Latex of -VC(50)-MMA(20)-EA(20)-AN(5)-AA(5)-(molecular weight: 80000)

P-10: Latex of -VDC(85)-MMA(5)-EA(5)-MAA(5)-(molecular weight: 67000)

P-11: Latex of -Et(90)-MAA(10)-(molecular weight: 12000)

P-12: Latex of -St(70)-2EHA(27)-AA(3)-(molecular weight: 130000)

P-13: Latex of -MMA(63)-EA(35)-AA(2)-(molecular weight: 33000)

Abbreviations used for the constituent monomers are as follows:

MMA: methyl methacrylate
EA: ethyl acrylate
MAA: methacrylic acid
2EHA: 2-ethylhexyl acrylate
St: styrene
Bu: butadiene
AA: acrylic acid
DVB: divinylbenzene
VC: vinyl chloride
AN: acrylonitrile
VDC: vinylidene chloride
Et: ethylene
IA: itaconic acid The polymer latexes mentioned above are also commercially available, and those mentioned below can be used, for example. Examples of acrylic resins are CEBIAN A-4635, 46583, 4601 (all from Daicel Chemical Industries), Nipol Lx811, 814, 821, 820, 857 (all from Nippon Zeon) etc.; examples of polyester resins are FINETEX ES650, 611, 675, 850 (all from Dai-Nippon Ink & Chemicals), WD-size, WMS (both from Eastman Chemical) etc.; examples of polyurethane resins are HYDRAN AP10, 20, 30, 40 (all from Dai-Nippon Ink & Chemicals) etc.; examples of rubber resins are LACSTAR 7310K, 3307B, 4700H, 7132C (all from Dai-Nippon Ink & Chemicals), Nipol Lx416, 410, 438C, 2507 (all from Nippon Zeon) etc.; examples of polyvinyl chloride resins are G351, G576 (both from Nippon Zeon) etc.; examples of polyvinylidene chloride resins are L502, L513 (both from Asahi Chemical Industry) etc.; examples of polyolefin resins are CHEMIPEARL S120, SA100 (both from Mitsui Petrochemical) etc.

These polymer latexes may be used each alone, or two or more kinds of them may be blended as required.

As the polymer latex used in the present invention, styrene/butadiene copolymer latex is particularly preferred. In the styrene/butadiene copolymer, the weight ratio of styrene monomer units to butadiene monomer units is preferably 40/60 to 95/5. The ratio of the styrene monomer units and the butadiene monomer units preferably account for from 60 to 99% by weight of the copolymer. The preferred range of the molecular weight of the copolymer is similar to that mentioned above.

Examples of styrene/butadiene copolymer latex preferably used for the present invention include the aforementioned P-3 to P-8, commercially available products, LACSTAR-3307B, 7132C, Nipol Lx416 and so forth.

The layer containing a silver salt of an organic acid of the thermally processed image recording material of the present invention may optionally be added with a hydrophilic polymer such as gelatin, polyvinyl alcohol, methylcellulose and carboxymethylcellulose. The amount of the hydrophilic polymer is preferably 30% by weight or less, more preferably 20% by weight or less, of the total binder in the layer containing silver salt of an organic acid.

The layer containing a silver salt of an organic acid (i.e., image-forming layer) is preferably formed by using polymer latex. The amount of the binder in the layer containing organic acid silver salt is such an amount that the weight ratio of total binder/organic acid silver salt should be 1/10 to 10/1, more preferably 1/5 to 4/1.

The layer containing a silver salt of an organic acid usually also serves as a photosensitive layer (emulsion layer) containing a photosensitive silver salt, that is, a photosensitive silver halide. In such a case, the weight ratio of total binder/silver halide is preferably 5 to 400, more preferably 10 to 200.

The total amount of the binder in the image-forming layer is preferably 0.2 to 30 g/m$^2$, more preferably 1 to 15 g/m$^2$, in terms of coating amount. The image-forming layer may optionally contain a crosslinking agent, a surfactant for improving coating property of the coating solution and so forth.

The solvent for the coating solution for the layer containing organic acid silver salt of the thermally processed image recording material of the invention (for simplicity, solvents and dispersion media are herein collectively referred to as "solvent") is preferably an aqueous solvent containing at least 30% by weight of water. As for components other than water, any water-miscible organic solvents may be used, including, for example, methyl alcohol, ethyl alcohol, isopropyl alcohol, methyl cellosolve, ethyl cellosolve, dimethylformamide, ethyl acetate and so forth. The water content of the solvent for the coating solution is preferably at least 50% by weight, more preferably at least 70% by weight. Preferred examples of the solvent composition are water, water/methyl alcohol=90/10, water/methyl alcohol=70/30, water/methyl alcohol/dimethylformamide=80/15/5, water/methyl alcohol/ethyl cellosolve=85/10/5, water/methyl alcohol/isopropyl alcohol=85/10/5 and so forth (numerals indicate weight %).

As antifoggants, stabilizers and stabilizer precursors that can be used for the present invention, there can be mentioned, for example, those mentioned in JP-A-10-62899, paragraph 0070 and EP 0803764A1, from page 20, line 57 to page 21, line 7. The antifoggants particularly preferably used in the present invention are organic halogenated compounds, and examples thereof include those disclosed in JP-A-11-65021, paragraphs 0111 to 0112. The organic halogenated compounds represented by the formula (P) mentioned in Japanese Patent Application No. 11-87297 and the organic polyhalogenated compounds represented by the general formula (II) mentioned in JP-A-10-339934 (specific examples are tribromomethylnaphthylsulfone, tribromomethylphenylsulfone, tribromomethyl(4-(2,4,6-trimethylphenylsulfonyl)phenyl)sulfone etc.) are particularly preferred.

The antifoggant is incorporated into the thermally processed image recording material by, for example, the method used for incorporating the aforementioned reducing agent, and the organic polyhalogenated compound is also preferably added as a solid microparticle dispersion.

Other examples of the antifoggant include the mercury(II) salts described in JP-A-11-65021, paragraph 0113, the benzoic acids described in the same, paragraph 0114, the salicylic acid derivatives represented by the formula (Z) mentioned in Japanese Patent Application No. 11-87297 and the formalin scavenger compounds represented by the formula (S) mentioned in Japanese Patent Application No. 11-23995.

The thermally processed image recording material of the invention may contain an azolium salt as the antifoggant. Examples of the azolium salt include, for example, the compounds of the general formula (XI) described in JP-A-59-193447, the compounds described in JP-B-55-12581 and the compounds of the general formula (II) described in JP-A-60-153039. The azolium salt may be present in any site of the thermally processed image recording material, but is preferably in a layer on the photosensitive layer side, more preferably in the layer containing the silver salt of an organic acid. The azolium salt may be added at any time during the preparation of the coating solution. When the azolium salt is added to the layer containing the silver salt of an organic acid, it may be added at any time during the period of from the preparation of the silver salt of an organic acid to the preparation of the coating solution. The azolium salt is preferably added during the period after the preparation of the silver salt of an organic acid and immediately before the coating. The azolium salt may be added in any form such as powder, solution and microparticle dispersion. It may also be added as a solution that also contains other additives such as sensitizing dye, reducing agent and toning agent. In the present invention, the amount of the azolium salt to be added is not particularly limited, but it is preferably $1 \times 10^{-6}$ mole to 2 moles, more preferably $1 \times 10^{-3}$ mole to 0.5 mole, per mole of silver.

The thermally processed image recording material of the invention may optionally contain any of mercapto compounds, disulfide compounds and thione compounds in order to control development by retarding or accelerating it, or enhance spectral sensitization efficiency, or improve storage stability before and after development. Examples of those compounds include, for example, those described in JP-A-10-62899, paragraphs 0067 to 0069, those of the formula (I) mentioned in JP-A-10-186572 and those mentioned in the paragraphs 0033 to 0052 of the same as specific examples, and those described in EP 0803764A1, page 20, lines 36 to 56. Among these, preferred are mercapto-substituted heteroaromatic compounds.

In the thermally processed image recording material of the present invention, it is preferable to add a toning agent. The toning agent is described in JP-A-10-62899, paragraphs 0054 to 0055, EP 0803764A1, page 21, lines 23 to 48 and Japanese Patent Application No. 10-213487. Preferred examples are phthalazinone, phthalazinone derivatives (e.g., 4-(1-naphthyl)phthalazinone, 6-chlorophthalazinone, 5,7-dimethoxyphthalazinone, 2,3-dihydro-1,4-phthalazinone and other derivatives) and metal salts thereof; combinations of phthalazinones and phthalic acid or derivatives thereof (e.g., phthalic acid, 4-methylphthalic acid, 4-nitrophthalic acid, tetrachlorophthalic anhydride etc.); phthalazines including phthalazine and phthalazine derivatives (e.g., 4-(1-naphthyl)-phthalazine, 6-isopropylphthalazine, 6-t-butylphthalazine, 6-chlorophthalazine, 5,7-dimethoxyphthalazine, 2,3-dihydrophthalazine and other derivatives) and metal salts thereof; combinations of phthalazines and phthalic acid or derivatives thereof (e.g., phthalic acid, 4-methylphthalic acid, 4-nitrophthalic acid, tetrachlorophthalic anhydride etc.). Particularly preferred are combinations of phthalazines and phthalic acid derivatives.

Plasticizers and lubricants that can be used for the photosensitive layer are described in JP-A-11-65021, paragraph 0117. Ultrahigh contrast agents for forming ultrahigh contrast images are described in the same publication, paragraph 0118, JP-A-11-223898, paragraphs 0136 to 0193, Japanese Patent Application No. 11-91652, general formula (H), formulas (1) to (3), formulas (A) and (B) and those mentioned in Japanese Patent Application No. 11-91652 as compounds of the general formulas (III) to (V) (specific compounds: Chem. 21 to Chem 24); and hardness enhancement promoters are described in JP-A-11-65021, paragraph 0102, and JP-A-11-223898, paragraphs 0194 to 0195. Addition methods and amounts of a nucleating agent are described in JP-A-11-223898, paragraphs 0182 to 0183. As for the ustrahigh contrast agent, preferred examples thereof include the following compounds.

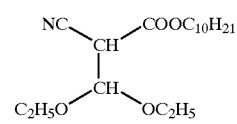

61

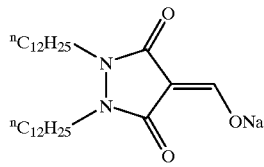

62

63

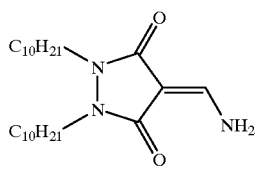

64

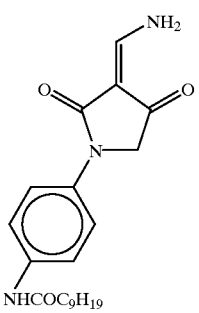

65

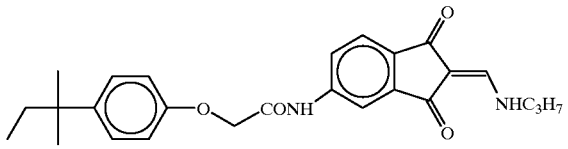

66

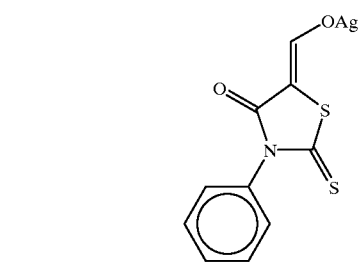

67

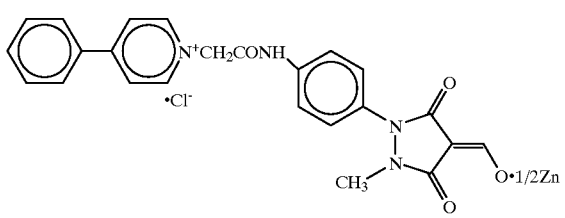

68

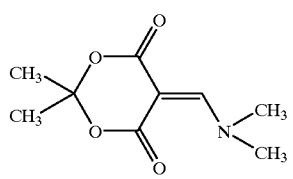

69

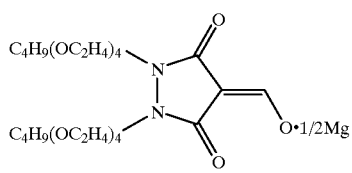

70

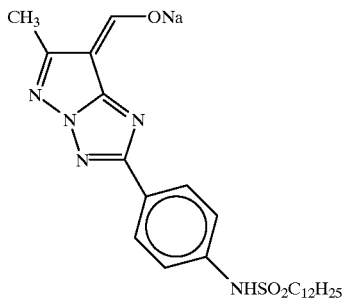

71

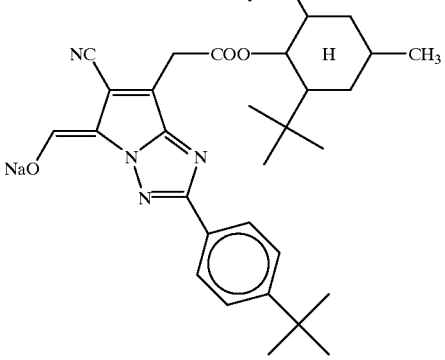

72

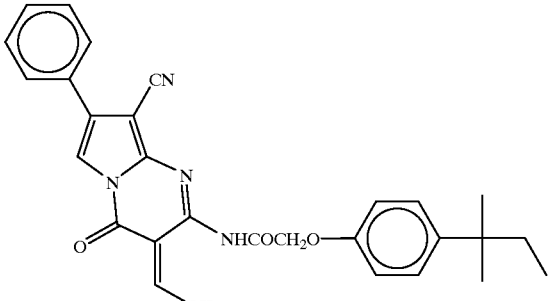

When formic acid or a formic acid salt is used as a strongly fogging substance, it is preferably used on the side having the image-forming layer containing a photosensitive silver halide in an amount of 5 mmol or less, more preferably 1 mmol or less, per 1 mole of silver.

When a nucleating agent is used in the thermally processed image recording material the present invention, an acid formed by hydration of diphosphorus pentoxide or a salt thereof is preferably used together with the nucleating agent. Examples of the acid formed by hydration of diphosphorus pentoxide or a salt thereof include metaphosphoric acid (salt), pyrophosphoric acid (salt), orthophosphoric acid (salt), triphosphoric acid (salt), tetraphosphoric acid (salt), hexametaphosphoric acid (salt) and so forth. Particularly preferably used acids formed by hydration of diphosphorus pentoxide or salts thereof are orthophosphoric acid (salt) and hexametaphosphoric acid (salt). Specific examples of the salt are sodium orthophosphate, sodium dihydrogenorthophosphate, sodium hexametaphosphate, ammonium hexametaphosphate and so forth.

The acid formed by hydration of diphosphorus pentoxide or a salt thereof may be used in a desired amount (coating amount per 1 m² of the thermally processed image recording material) depending on the desired performance including sensitivity and fog. However, it can be used in an amount of preferably 0.1–500 mg/m²₁ more preferably 0.5–100 mg/m².

The thermally processed image recording material of the present invention may be provided with a surface protective layer, for example, to prevent adhesion of the image-forming layer. The surface protective layer is described in, for example, JP-A-11-65021, paragraphs 0119 to 0120.

While gelatin is preferred as the binder in the surface protective layer, polyvinyl alcohol (PVA) is also preferably used. Examples of PVA include, for example, completely saponified PVA-105, partially saponified PVA-205, PVA-335, MP-203 that is denatured polyvinyl alcohol (all from Kraray Co., Ltd.) and so forth. The application amount of the polyvinyl alcohol (per m² of the support) for protective layers is preferably 0.3 to 4.0 g/m², more preferably 0.3 to 2.0 g/m² (per one layer).

When the thermally processed image recording material of the present invention is used for printing use is which dimensional change is critical, in particular, polymer latex is preferably used also in a protective layer or a back layer. Such latex is described in "Gosei Jushi Emulsion (Synthetic Resin Emulsion)", compiled by Taira Okuda and Hiroshi Inagaki, issued by Kobunshi Kanko Kai (1978); "Gosei Latex no Oyo (Application of Synthetic Latex) ", compiled by Takaaki Sugimura, Yasuo Kataoka, Souichi Suzuki and Keishi Kasahara, issued by Kobunshi Kanko Kai (1993); Soichi Muroi, "Gosei Latex no Kagaku (Chemistry of Synthetic Latex) ", Kobunshi Kanko Kai (1970) and so forth. Specific example thereof include latex of methyl methacrylate (33.5 weight %)/ethyl acrylate (50 weight %)/methacrylic acid (16.5 weight %) copolymer, latex of methyl methacrylate (47.5 weight %)/butadiene (47.5 weight %)/itaconic acid (5 weight %) copolymer, latex of ethyl acrylate/methacrylic acid copolymer, latex of methyl methacrylate (58.9 weight %)/2-ethylhexyl acrylate (25.4 weight %)/styrene (8.6 weight %)/2-hydroxyethyl methacrylate (5.1 weight %)/acrylic acid (2.0 weight %) copolymer and so forth. As for the binder of the protective layer, there may be used the combination of polymer latex disclosed in Japanese Patent Application No. 11-6872, and techniques disclosed in Japanese Patent Application No. 11-143058, paragraphs 0021–0025, Japanese Patent Application No. 11-6872, paragraphs 0027–0028, and Japanese Patent Application No. 11-199626, paragraphs 0023–0041.

The temperature for preparation of the coating solution for the image-forming layer used for the present invention may preferably be 30° C. to 65° C., more preferably 35° C. to 60° C., most preferably 35° C. to 55° C. The temperature of the coating solution for image-forming layer immediately after the addition of the polymer latex may preferably be kept at 30° C. to 65° C. A reducing agent and a silver salt of an organic acid are preferably mixed before the addition of polymer latex.

The fluid containing silver salt of organic acid or coating solution for the image-forming layer is preferably a so-called thixotropic fluid. Thixotropy means that viscosity of a fluid lowers with increase of shear rate. Any apparatus may be used for measurement of viscosity, and for example, RFS Fluid Spectrometer from Rheometrics Far East Co., Ltd. is preferably used and the measurement is performed at 25° C. Viscosity of the fluid containing silver salt of organic acid or coating solution for the image-forming layer is preferably 400–100,000 mPa·s, more preferably 500–20,000 mPa·s, at a shear rate of 0.1 sec⁻¹. The viscosity is preferably 1–200 mPa·s, more preferably 5–80 mPa·s, at a shear rate of 1000 sec⁻¹.

Various systems exhibiting thixotropic property are known and, for example, described in "Koza Rheology (Lecture on Rheology)", Kobunshi Kanko Kai; Muroi & Morino, "Kobunshi Latex (Polymer Latex)", Kobunshi Kanko Kai and so forth. A fluid is required to contain a large amount of solid microparticles to exhibit thixotropic property. For enhancing thixotropic property, it is effective that the fluid is added with a viscosity-increasing linear polymer, or solid microparticles to be contained have anisotropic shapes and an increased aspect ratio. Use of an alkaline viscosity-increasing agent or a surfactant is also effective for that purpose.

The thermally processed image recording material of the present invention is constituted by one or more layers on a support. When it is constituted with a monolayer, the layer must contain a silver salt of an organic acid, silver halide, developing agent and binder as well as desired additional materials such as toning agent, coating aid and other auxiliary agents. When the layer is bilayer, the first emulsion layer (in general, the layer adjacent to the support) must contain a silver salt of an organic acid and silver halide, and the second emulsion layer or the both layers must contain the other ingredients. Another type of bilayer structure is also employable in which one layer is a single emulsion layer containing all necessary ingredients and the other layer is a protective top coat layer. Multicolor thermally processed image recording material may contain these two layers for each color, or may contain all necessary ingredients in a single layer as described in U.S. Pat. No. 4,708,928. As for multicolor thermally processed image recording material containing multiple dyes, each emulsion layers are kept individually by using a functional or non-functional barrier layer between the adjacent photosensitive layers as described in U.S. Pat. No. 4,460,681.

For the photosensitive layer, various types of dyes and pigments may be used to improve color tone, to prevent interference fringes generated during laser exposure, and to prevent irradiation. These techniques are detailed in International Patent Publication WO98/36322.

In the thermally processed image recording material of the present invention, an antihalation layer may be provided in a distant position from a light source relative to the photosensitive layer. The antihalation layer is described in JP-A-11-65021, paragraphs 0123 to 0124, JP-A-11-223898 etc.

Thermally processed image recording materials generally have non-photosensitive layers in addition to the photosensitive layers. Depending on their positions, the non-photosensitive layers are classified into (1) a protective layer to be provided on a photosensitive layer (the opposite side of the support); (2) an intermediate layer to be provided between two or more of photosensitive layers or between a photosensitive layer and a protective layer; (3) an undercoat layer to be provided between a photosensitive layer and a support; (4) a back layer to be provided on a side opposite to the photosensitive layer. A filter layer is provided in the photosensitive material as the layer (1) or (2). The antihalation layer is provided in the thermally processed image recording material as the layer (3) or (4).

When a dye exhibiting absorption in the visible region is used for antihalation, a thermally decoloring dye and a base precursor are preferably added to a non-photosensitive layer so that the non-photosensitive layer can function as a filter layer or an antihalation layer.

The thermally decoloring dye and the base precursor are preferably added to the same non-photosensitive layer. They may be also added separately to adjacent two non-photosensitive layers. If desired, a barrier layer may be provided between the two non-photosensitive layers.

As methods to add a thermally decoloring dye to a non-photosensitive layer, a method may be employed which comprises step of adding a solution, emulsion, solid or microparticle dispersion of the dye, or the dye impregnated in a polymer to a coating solution for the non-photosensitive layer. The dye may also be added to the non-photosensitive layer by using a polymer mordant. These addition methods are the same as those generally employed for the addition of dyes to ordinary thermally processed image recording materials. Polymer latex used for preparation of the dye impregnated in a polymer are described in U.S. Pat. No. 4,199,363, German Patent Laid-open Nos. 25,141,274, 2,541,230, EP-A-029104 and JP-B-53-41091. An emulsification method by adding a dye to a solution in which a polymer is dissolved is described in International Patent Publication WO88/00723.

The amount of the decoloring dye may be determined depending on purpose of the use of the dye. In general, the dye is used in an amount to give an optical density (absorbance) of larger than 0.1 measured at an intended wavelength. The optical density is preferably 0.2 to 2. The amount of the dye to give such optical density may be generally from about 0.001 to about 1 g/m$^2$.

Decoloring of dyes in that manner can lower optical density of the material to 0.1 or less. Two or more different decoloring dyes may be used in the thermally decoloring type recording materials or thermally processed image recording materials. Similarly, two or more different base precursors may be used in combination.

The thermally processed image recording material of the present invention is preferably a so-called single-sided photosensitive material comprising at least one photosensitive layer containing a silver halide on one side of support, and a backing layer on the other side.

The thermally processed image recording material of the present invention may preferably contain a matting agent for improving the transferability of the material. Matting agents are described in JP-A-11-65021, paragraphs 0126 to 0127. The matting agent is added in an amount of preferably 1 to 400 mg/m$^2$, more preferably 5 to 300 mg/m$^2$, as the amount per 1 m$^2$ of the photosensitive material.

While the matting degree of the surface of the image-forming layer side is not particularly limited so long as the material is free from stardust defects, Beck's smoothness of the surface is preferably 30 seconds to 2000 seconds, more preferably 40 seconds to 1500 seconds. Beck smoothness can be easily determined by Japanese Industrial Standard (JIS) P8119, "Test Method for Smoothness of Paper and Paperboard by Beck Test Device" and TAPPI Standard Method T479.

In the present invention, the matting degree of the back layer is preferably in the range of 10–1200 seconds, more preferably 30–700 seconds, further preferably 50–500 seconds as shown by the Beck's smoothness.

In the present invention, the matting agent may preferably be contained in the outermost surface layer, or in a layer functioning as an outermost surface layer, or in a layer near to the outer surface of the thermally processed image recording material. The agent may also be preferably contained in a layer functioning as a protective layer.

The back layers that can be used in the present invention are described in JP-A-11-65021, paragraphs 0128 to 0130.

The thermally processed image recording material of the present invention preferably has a film surface pH of 6.0 or less, more preferably 5.5 or less, before heat development. While the lower limit is not particularly limited, it is normally around 3. For controlling the film surface pH, an organic acid such as phthalic acid derivatives or a nonvolatile acid such as sulfuric acid, and a volatile base such as ammonia are preferably used to control the film surface pH. In particular, ammonia is preferred to achieve a low film surface pH, because it is highly volatile and therefore it can be removed before coating or heat development. A method for measuring the film surface pH is described in Japanese Patent Application No. 11-87297, paragraph 0123.

A hardening agent may be added to the photosensitive layer, protective layer, back layer, and other layers. Examples of the hardening agent are described in T. H. James, "THE THEORY OF THE PHOTOGRAPHIC PROCESS, FOURTH EDITION", Macmillan Publishing Co., Inc., 1977, pp. 77–87. Polyvalent metal ions described on page 78 of the above article, polyisocyanates described in U.S. Pat. No. 4,281,060 and JP-A-6-208193; epoxy compounds described in U.S. Pat. No. 4,791,042; vinylsulfone compounds described in JP-A-62-89048 and so forth may preferably be used.

The hardening agent is added to coating solutions as a solution. Preferred addition time of the solution to the coating solution of the protective layer resides in a period of from 180 minutes before the coating to just before the coating, preferably 60 minutes to 10 seconds before the coating. The method and conditions for mixing are not particularly limited so long as the effect of the present invention can be obtained satisfactorily. Specific examples of the mixing method include a method in which a mixing is performed in a tank designed so as to obtain a desired average residence time which is calculated from addition flow rate and feeding amount to a coater, a method utilizing a static mixer described in N. Harnby, M. F. Edwards, A. W. Nienow, "Ekitai Kongo Gijutsu (Techniques for Mixing Liquids)", translated by Koji Takahashi, Chapter 8, Nikkan Kogyo Shinbunsha, 1989 and so forth.

Surfactants that can be used in the present invention are described in JP-A-11-65021, paragraph 0132; usable solvents are described in the above patent document in paragraph 0133; usable supports are described in the above patent document in paragraph 0134; usable antistatic and electroconductive layers are described in the above patent document in paragraph 0135; usable methods for forming color images are described in the above patent document in paragraph 0136; usable lubricants are described in JP-A-11-84573, paragraphs 0061 to 0064 and Japanese Patent Application No. 11-106881, paragraphs 0049 to 0062.

Preferably used as a transparent support is a polyester film, in particular, polyethylene terephthalate film, subjected to a heat treatment in a temperature range of 130–185° C. in order to relax the internal distortion formed in the film during the biaxial stretching so that thermal shrinkage distortion occurring during the heat development could be eliminated. When the thermally processed image recording material is for medical use, the transparent support may be colored with blue dyes (e.g., Dye-1 described in Examples of JP-A-8-240877), or may be colorless. For the support, techniques for undercoating described in JP-A-11-84574 (utilizing water-soluble polyester), JP-A-10-186565 (utilizing styrene/butadiene copolymer), Japanese Patent Application No. 11-106881, paragraphs 0063–0080 (utilizing vinylidene chloride copolymer) and so forth are preferably used. As for antistatic layers and undercoating, techniques disclosed in JP-A-56-143430, JP-A-56-143431, JP-A-58-62646, JP-A-56-120519, JP-A-11-84573, paragraphs 0040–0051, U.S. Pat. No. 5,575,957 and JP-A-11-223898, paragraphs 0078–0084 can also be used.

The thermally processed image recording material of the present invention is preferably of a monosheet type. The monosheet type does not use any additional sheets such as image receiving materials, but can form images directly on the thermally processed image recording material itself.

The thermally processed image recording material may further contain an antioxidant, stabilizer, plasticizer, UV absorber or coating aid. Such various additives may be added to any of photosensitive layers or non-photosensitive layers. For these additives, International Patent Publication WO98/36322, EP803764A1, JP-A-10-186567, JP-A-10-18568 and so forth may be referred to.

The coating method used for the production of the thermally processed image recording material of the present invention is not particularly limited, and any coating method can be used. Specific examples thereof include, for example, extrusion coating, slide coating, curtain coating, dip coating, knife coating, flow coating, extrusion coating utilizing a hopper of the type described in U.S. Pat. No. 2,681,294 and so forth. Preferably used are extrusion coating and slide coating described in Stephen F. Kistler, Petert M. Schweizer, "LIQUID FILM COATING", published by CHAPMAN & HALL Co., Ltd., 1997, pp.399–536, and particularly preferably used is the slide coating. An example of the shape of a slide coater used for the slide coating is shown in FIG. 11b, 1, on page 427 of the aforementioned reference. If desired, two or more layers may be formed at the same time, for example, according to the methods described in the aforementioned reference, from page 399 to page 536, or the methods described in U.S. Pat. No. 2,761,791 and British Patent No. 837,095.

Other techniques that can be used for the production of the thermally processed image recording material of the present invention are also described in EP803764A1, EP883022A1, WO98/36322, JP-A-56-62648, JP-A-58-62644, JP-A-9-281637, JP-A-9-297367, JP-A-9-304869, JP-A-9-311405, JP-A-9-329865, JP-A-10-10669, JP-A-10-62899, JP-A-10-69023, JP-A-10-186568, JP-A-10-90823, JP-A-10-171063, JP-A-10-186565, JP-A-10-186567, JP-A-10-186569, JP-A-10-186570, JP-A-10-186571, JP-A-10-186572, JP-A-10-197974, JP-A-10-197982, JP-A-10-197983, JP-A-10-197985, JP-A-10-197986, JP-A-10-197987, JP-A-10-207001, JP-A-10-207004, JP-A-10-221807, JP-A-10-282601, JP-A-10-288823, JP-A-10-288824, JP-A-10-307365, JP-A-10-312038, JP-A-10-339934, JP-A-11-7100, JP-A-11-15105, JP-A-11-24200, JP-A-11-24201, JP-A-11-30832, JP-A-11-84574, JP-A-11-65021, JP-A-11-109547, JP-A-11-125880, JP-A-11-129629, JP-A-11-133536, JP-A-11-133537, JP-A-11-133538, JP-A-11-133539, JP-A-11-133542, JP-A-11-133543 and JP-A-11-223898.

The thermally processed image recording material of the invention may be developed in any manner. However, an imagewise exposed thermally processed image recording material is usually developed by heating. The temperature for the heat development is generally about 80° C. to 250° C., more preferably 100° C. to 140° C. The development time is preferably 1 to 180 seconds, more preferably 10 to 90 seconds, particularly preferably 10 to 40 seconds.

For thermal development for the material, preferred is a plate heater system. For heat development by the plate heater system, the method described in JP-A-11-133572 is preferred. The plate heater system described in this reference is a heat development apparatus wherein a thermally processed image recording material on which a latent image is formed is brought into contact with a heating means in a heat development section to obtain a visible image. In this apparatus, the heating means comprises a plate heater, and a plurality of presser rollers are disposed facing to one surface of the plate heater. Heat development of the thermally processed image recording material is attained by passing the material between the presser rollers and the plate heater. The plate heater is preferably sectioned into 2 to 6 stages, and the temperature of the top stage is preferably kept lower by 1 to 10° C. or so than that of the others. Such a method is also described in JP-A-54-30032. Such a plate heater system can remove moisture and organic solvent contained in the thermally processed image recording material out of the material, and prevent deformation of the support of the thermally processed image recording material caused by rapidly heating the material.

The thermally processed image recording material of the present invention can be exposed in any manner. As light source of exposure, laser rays are preferred. As the laser used in the present invention, gas lasers ($Ar^+$, He—Ne), YAG lasers, dye lasers, semiconductor lasers and so forth are preferred. A combination of semiconductor laser and second harmonic generating device or the like may also be used. Preferred are gas or semiconductor lasers for red to infrared emission.

As a laser imager provided with a light exposure section and a heat development section, Fuji Medical Dry Laser Imager FM-DP L can be mentioned. FM-DP L is explained in Fuji Medical Review, No. 8, pages 39–55, and those techniques described therein can of course be used in laser imagers for the thermally processed image recording material of the present invention.

The thermally processed image recording material of the invention forms a monochromatic image based on silver image, and is preferably used as thermally processed image recording materials for use in medical diagnosis, industrial photography, printing and COM.

EXAMPLES

The present invention will be specifically explained with reference to the following examples. The materials, regents, ratios, procedures and so forth shown in the following examples can be optionally changed so long as such change does not depart from the spirit of the present invention. Therefore, the scope of the present invention is not limited by the following examples.

Example 1

Synthesis of Exemplary Compound 1

Bis-1,1-(2-hydroxy-3,5-dimethylphenyl)-3,5,5-trimethylhexane (11.0 g) and triphenylphosphine oxide (7.4 g) were dissolved in ethyl acetate (7 ml) with heating, and the solution was added with hexane and left standing at room temperature. The crystals were taken by filtration and washed with hexane to obtain Exemplary Compound 1 (17.8 g). Melting point: 114–115° C.

Example 2

Synthesis of Exemplary Compound 2

2,2'-Isobutylidenebis-4,6-dimethylphenol (9.7 g) and triphenylphosphine oxide (9.0 g) were dissolved in ethyl acetate (12 ml) with heating, and the solution was added with hexane and left standing at room temperature. The crystals were taken by filtration and washed with hexane to obtain Exemplary Compound 2 (15.0 g). Melting point: 132–133° C.

Example 3
Synthesis of Exemplary Compound 3

2,2'-Butylidenebis(6-t-butyl-4-methylphenol) (5.0 g) and triphenylphosphine oxide (3.6 g) were dissolved in ethyl acetate (3 ml) with heating, and the solution was added with hexane and left standing at room temperature. The crystals were taken by filtration and washed with hexane to obtain Exemplary Compound 3 (6.5 g). Melting point: 138–139° C.

Example 4
Synthesis of Exemplary Compound 4

2,2'-Methylenebis(6-t-butyl-4-methylphenol) (11.0 g) and triphenylphosphine oxide (9.0 g) were dissolved in ethyl acetate (5 ml) with heating, and the solution was added with hexane and left standing at room temperature. The crystals were taken by filtration and washed with hexane to obtain Exemplary Compound 4 (18.3 g). Melting point: 124–126° C.

The result of X-ray crystal diffraction analysis of the synthesized Exemplary Compound 4 obtained by using a tetraxial X-ray crystal diffraction measurement apparatus (Rigaku Denki, AFC-5R) is shown in FIG. 1.

Example 5
Synthesis of Exemplary Compound 8

2,2'-Methylenebis(6-t-butyl-4-ethylphenol) (11.0 g) and triphenylphosphine oxide (11.0 g) were dissolved in ethyl acetate (5 ml) with heating, and the solution was added with hexane and left standing at room temperature. The crystals were taken by filtration and washed with hexane to obtain Exemplary Compound 8 (18.5 g). Melting point: 112–114° C.

Example 6
Preparation of photothermographic material

Structures of the compounds used in Example 6 are shown below.

Spectral Sensitizing Dye A

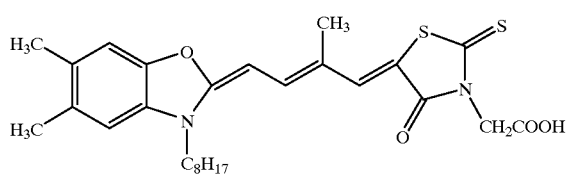

Tellurium Sensitizer B

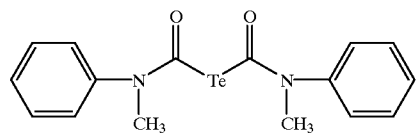

Base Precursor Compound 11

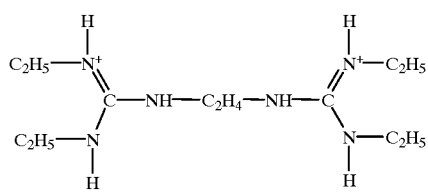

-continued

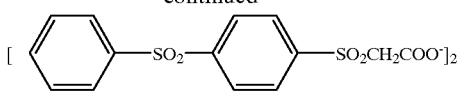

Cyanine Dye Compound 13

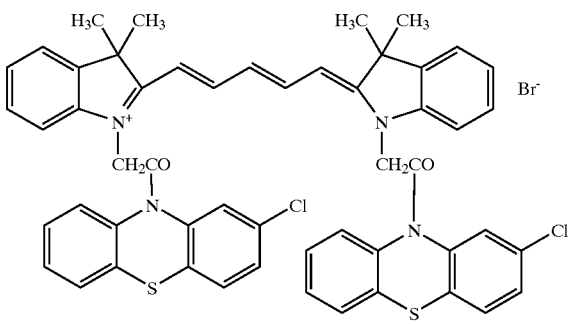

Blue Dye Compound 14

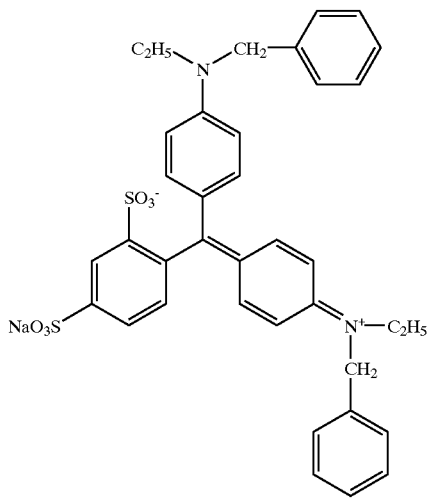

<<Preparation of PET support>>

Using terephthalic acid and ethylene glycol, PET having an intrinsic viscosity IV of 0.66 (measured in phenol/tetrachloroethane=6/4 (weight ratio) at 25° C.) was obtained in a conventional manner. The PET was pelletized, and the pellets were dried at 130° C. for 4 hours, melted at 300° C., then extruded from a T-die, and quenched to prepare an unstretched film having such a thickness that the film thickness after thermal fixation should become 175 μm.

The film was stretched along the longitudinal direction by 3.3 times using rollers having different peripheral speeds and then stretched along the transverse direction by 4.5 times using a tenter. In this case, the temperatures were 110° C. and 130° C., respectively. Thereafter, the film was subjected to thermal fixation at 240° C. for 20 seconds and relaxed by 4% along the transverse direction at the same temperature. Then, after chucks of the tenter were released, the both edges of the film were knurled, and the film was rolled up at 4 kg/cm² to provide a roll of the film having a thickness of 175 μm.

<<Surface corona discharging treatment>>

Using a solid state corona discharging treatment machine Model 6KVA manufactured by Piller Inc., both surfaces of the support were treated at room temperature at 20 m/minute. In this case, from the read out values of the electric current and voltage, it was seen that the treatment of 0.375 kV·A·minute/m² was applied to the support. The treated frequency in this case was 9.6 kHz and the gap clearance between the electrode and the dielectric roll was 1.6 mm.

<<Preparation of undercoated support>>

(1) Preparation of coating solutions for undercoat layers

| Formulation (1) (for undercoat layer on photosensitive layer side) | |
|---|---|
| Pesresin A-515GB made by Takamatsu Yushi K.K. (30 weight % solution) | 234 g |
| Polyethylene glycol monononylphenyl ether (mean ethylene oxide number = 8.5, 10 weight % solution) | 21.5 g |
| MP-1000 made by Soken Kagaku K.K. (polymer microparticles, mean particle size: 0.4 μm) | 0.91 g |
| Distilled water | 744 ml |
| Formulation (2) (for 1st layer on back surface) | |
| Butadiene-styrene copolymer latex (solid content: 40 weight %, weight ratio of butadiene/styrene = 32/68) | 158 g |
| 2,4-Dichloro-6-hydroxy-S-triazine sodium salt (8 weight % aqueous solution) | 20 g |
| 1 weight % Aqueous solution of sodium laurylbenzenesulfonate | 10 ml |
| Distilled water | 854 ml |
| Formulation 3 (for 2nd layer on back surface side) | |
| $SnO_2/SbO$ (weight ratio: 9/1, mean particle size: 0.038 μm, 17 weight % dispersion) | 84 g |
| Gelatin (10% aqueous solution) | 89.2 g |
| Metorose TC-5 made by Shin-Etsu Chemical Co., Ltd. (2% aqueous solution) | 8.6 g |
| MP-1000 (polymer microparticles) made by Soken Kagaku K.K. | 0.01 g |
| 1 weight % Aqueous solution of sodium dodecylbenzenesulfonate | 10 ml |
| NaOH (1%) | 6 ml |
| Proxel (made by ICI Co.) | 1 ml |
| Distilled water | 805 ml |

<<Preparation of undercoated support>>

After applying the aforementioned corona discharging treatment to both surfaces of the aforementioned biaxially stretched polyethylene terephthalate support having a thickness of 175 μm, one surface (photosensitive layer side) thereof was coated with the undercoating solution of Formulation (1) by a wire bar in a wet coating amount of 6.6 ml/m² (per one surface) and dried at 180° C. for 5 minutes. Then, the back surface thereof was coated with the undercoating solution of Formulation (2) by a wire bar in a wet coating amount of 5.7 ml/m² and dried at 180° C. for 5 minutes. The back surface thus coated was further coated with the undercoating solution of Formulation (3) by a wire bar in a wet coating amount of 7.7 ml/m² and dried at 180° C. for 6 minutes to prepare an undercoated support.

<<Preparation of coating solution for back surface>>

(Preparation of Solid microparticle dispersion (a) of base precursor)

64 g of Base precursor compound 11, 28 g of diphenylsulfone and 10 g of a surface active agent, Demor N (manufactured by Kao Corporation), were mixed with 220 ml of distilled water, and the mixture was beads-dispersed using a sand mill (¼ Gallon Sand Grinder Mill, manufactured by Imex Co.) to obtain Solid microparticle dispersion (a) of the base precursor compound having a mean particle size of 0.2 μm.

<<Preparation of dye solid microparticle dispersion>>

9.6 g of Cyanine dye compound 13 and 5.8 g of sodium p-dodecylbenzenesulfonate were mixed with 305 ml of distilled water, and the mixture was beads-dispersed using a sand mill (¼ Gallon Sand Grinder Mill, manufactured by Imex Co.) to obtain a dye solid microparticle dispersion having a mean particle size of 0.2 μm.

<<Preparation of coating solution for antihalation layer>>

17 g of gelatin, 9.6 g of polyacrylamide, 70 g of the aforementioned Solid microparticle dispersion (a) of the base precursor, 56 g of the aforementioned dye solid microparticle dispersion, 1.5 g of polymethyl methacrylate microparticles (mean particle size 6.5 μm), 0.03 g of benzoisothiazolinone, 2.2 g of sodium polyethylenesulfonate, 0.2 g of Blue dye compound 14 and 844 ml of water were mixed to prepare a coating solution for antihalation layer.

<<Preparation of coating solution for back surface protective layer>>

In a container kept at 40° C., 50 g of gelatin, 0.2 g of sodium polystyrenesulfonate, 2.4 g of N,N-ethylenebis (vinyl-sulfonacetamide), 1 g of sodium t-octylphenoxyethoxyethane-sulfonate, 30 mg of benzoisothiazolinone, 37 mg of N-perfluorooctylsulfonyl-N-propylalanine potassium salt, 0.15 g of polyethylene glycol mono(N-perfluorooctylsulfonyl-N-propyl-2-aminoethyl) ether [average polymerization degree of ethylene oxide: 15], 32 mg of $C_8F_{17}SO_3K$, 64 mg of $C_8F_{17}SO_2N(C_3H_7)(CH_2CH_2O)_4(CH_2)_4SO_3Na$, 8.8 g of an acrylic acid/ethyl acrylate copolymer (copolymerization ratio (by weight): 5/95), 0.6 g of Aerosol OT (manufactured by American Cyanamid Company), 1.8 g (as liquid paraffin) of a liquid paraffin emulsion and 950 ml of water were mixed to form a coating solution for back surface protective layer.

<<Preparation of silver halide emulsion 1>>

1421 ml of distilled water was added with 8.0 ml of 1 weight % potassium bromide solution, and further added with 8.2 ml of 1 N nitric acid and 20 g of phthalized gelatin. Separately, Solution A was prepared by adding distilled water to 37.04 g of silver nitrate to dilute it to 159 ml, and Solution B was prepared by diluting 32.6 g of potassium bromide with distilled water to a volume of 200 ml. To the aforementioned mixture maintained at 37° C. and stirred in a titanium-coated stainless steel reaction vessel, the whole volume of Solution A was added by the control double jet method over 1 minute at a constant flow rate while pAg was maintained at 8.1. Solution B was also added by the control double jet method. Then, the mixture was added with 30 ml of 3.5 weight % aqueous hydrogen peroxide solution, and further added with 36 ml of 3 weight % aqueous solution of benzimidazole. Separately, Solution A2 was prepared by diluting Solution A with distilled water to a volume of 317.5 ml, and Solution B2 was prepared by dissolving tripotassium hexachloroiridate in Solution B in such an amount that its final concentration should become $1 \times 10^{-4}$ mole per mole of silver, and diluting the obtained solution with distilled water to a volume twice as much as the volume of Solution B, i.e., 400 ml. The whole volume of Solution A2 was added to the mixture again by the control double jet method over 10 minutes at a constant flow rate while pAg was maintained at 8.1. Solution B2 was also added by the control double jet method. Then, the mixture was added with 50 ml of a 0.5 weight % solution of 2-mercapto-5-methylbenzimidazole in methanol. After pAg was raised to 7.5 with silver nitrate, the mixture was adjusted to pH 3.8 with 1 N sulfuric acid, and the stirring was stopped. Then, the mixture was subjected to precipitation, desalting and washing with water, added with 3.5 g of deionized gelatin and 1 N sodium hydroxide to be adjusted to pH 6.0 and pAg of 8.2 to form a silver halide dispersion.

The grains in the completed silver halide emulsion were pure silver bromide grains having a mean diameter of 0.053 µm as spheres and a variation coefficient of 18% for the diameter as spheres. The grain size and others were obtained from averages for 1000 grains by using an electron microscope. The [100] face ratio of these grains was determined to be 85% by the Kubelka-Munk method.

The aforementioned emulsion was added with 0.035 g of benzoisothiazolinone (added as a 3.5 weight % methanol solution of the compound) with stirring at 38° C., after 40 minutes since then, added with the solid dispersion (an aqueous gelatin solution) of Spectral sensitizing dye A in an amount of $5 \times 10^{-3}$ mole per mole of silver. After 1 minute, the mixture was warmed to 47° C., and after 20 minutes, added with $3 \times 10^{-5}$ mole of sodium benzenethiosulfonate per mole of silver. Further after 2 minutes, the mixture was added with Tellurium sensitizer B in an amount of $5 \times 10^{-5}$ mole per mole of silver followed by ripening for 90 minutes. Immediately before finishing the ripening, the mixture was added with 5 ml of 0.5 weight % methanol solution of N,N'-dihydroxy-N'-diethylmelamine, and after lowering the temperature to 31° C., added with 5 ml of 3.5 weight % methanol solution of phenoxyethanol, $7 \times 10^{-3}$ mole of 5-methyl-2-mercaptobenzimidazole per mole of silver and $6.4 \times 10^{-3}$ mole of 1-phenyl-2-heptyl-5-mercapto-1,3,4-triazole per mole of silver to prepare Silver halide emulsion 1.

<<Preparation of Silver halide emulsion 2>>

In the same manner as the preparation of Silver halide emulsion 1 except that the liquid temperature upon forming the grains was changed from 37° C. to 50° C., an emulsion of pure silver bromide cubic grains having a mean grain size of 0.08 µm as spheres and a variation coefficient of 15% for size as spheres was prepared. Further, as in the case of Silver halide emulsion 1, the steps of precipitation, desalting, washing with water and dispersion were performed. Furthermore, in the same manner as in the case of Silver halide emulsion 1 except that the addition amount of Spectral sensitizing dye A was changed to $4.5 \times 10^{-3}$ mole per mole of silver, the spectral sensitization, chemical sensitization and addition of 5-methyl-2-mercaptobenzimidazole and 1-phenyl-2-heptyl-5-mercapto-1,3,4-traizole were performed to obtain Silver halide emulsion 2.

<<Preparation of Silver halide emulsion 3>>

In the same manner as the preparation of Silver halide emulsion 1 except that the liquid temperature upon forming the grains was changed from 37° C. to 27° C., an emulsion of pure silver bromide cubic grains having a mean grain size of 0.038 µm as spheres and a variation coefficient of 20% for size as spheres was prepared. Further, as in the case of Silver halide emulsion 1, the steps of precipitation, desalting, washing with water and dispersion were performed. Furthermore, in the same manner as in the case of Silver halide emulsion 1 except that the addition amount of Spectral sensitizing dye A was changed to $6 \times 10^{-3}$ mole per mole of silver, the spectral sensitization, chemical sensitization and addition of 5-methyl-2-mercaptobenzimidazole and 1-phenyl-2-heptyl-5-mercapto-1,3,4-traizole were performed to obtain Silver halide emulsion 3.

<<Preparation of Mixed emulsion A for coating solution>>

70% by weight of Silver halide emulsion 1, 15% by weight of Silver halide emulsion 2 and 15% by weight of Silver halide emulsion 3 were mixed and added with benzothiazolium iodide in an amount of $7 \times 10^{-3}$ mole per mole of silver as a 1 weight % aqueous solution to form Mixed emulsion A for coating solution.

<<Preparation of scaly silver behenate dispersion>>

87.6 kg of behenic acid (Edenor C22-85R, trade name, manufactured by Henkel Co.), 423 liters of distilled water, 49.2 liters of a 5 N aqueous solution of NaOH, and 120 liters of tert-butanol were mixed and allowed to react by stirring at 75° C. for one hour to obtain a solution of sodium behenate. Separately, 206.2 liters of an aqueous solution containing 40.4 kg of silver nitrate (pH 4.0) was prepared and kept at 10° C. A mixture of 635 liters of distilled water and 30 liters of tert-butanol contained in a reaction vessel kept at 30° C. was added with the whole amount of the aforementioned sodium behenate solution and the whole amount of the aqueous silver nitrate solution with stirring at constant flow rates over the periods of 62 minutes and 10 seconds, and 60 minutes, respectively. In this case, the aqueous silver nitrate solution was added in such a manner that only the aqueous silver nitrate solution should be added for 7 minutes and 20 seconds after starting the addition of the aqueous silver nitrate solution, and then the addition of the aqueous solution of sodium behenate was started and added in such a manner that only the aqueous solution of sodium behenate should be added for 9 minutes and 30 seconds after finishing the addition of the aqueous silver nitrate solution. In this operation, the outside temperature was controlled so that the temperature in the reaction vessel could be 30° C. and the liquid temperature should be constant. The piping of the addition system for the sodium behenate solution was warmed by steam trace and the steam opening was controlled such that the liquid temperature at the outlet orifice of the addition nozzle should be 75° C. The piping of the addition system for the aqueous silver nitrate solution was maintained by circulating cold water outside a double pipe. The addition position of the sodium behenate solution and the addition position of the aqueous silver nitrate solution were arranged symmetrically with respect to the stirring axis as the center, and the positions are controlled to be at heights for not contacting with the reaction mixture.

After finishing the addition of the sodium behenate solution, the mixture was left with stirring for 20 minutes at the same temperature and then the temperature was decreased to 25° C. Thereafter, the solid content was recovered by suction filtration and washed with water until electric conductivity of the filtrate became 30 µS/cm. Thus, an silver salt of an organic acid was obtained. The solid content was stored as a wet cake without being dried.

When the shape of the obtained silver behenate grains was evaluated by an electron microscopic photography, the grains were scaly crystals having a =0.14 µm, b =0.4 µm, and c =0.6 µm in mean values, a mean aspect ratio of 5.2, a mean diameter as spheres of 0.52 µm, and a variation coefficient of 15% for mean diameter as spheres (a, b and c have the meanings defined in the present specification).

To the wet cake corresponding to 100 g of the dry solid content was added with 7.4 g of polyvinyl alcohol (PVA-217, trade name) and water to make the total amount 385 g, and the mixture was pre-dispersed by a homomixer.

Then, the pre-dispersed stock dispersion was treated three times by using a dispersing machine (Microfluidizer M-110S-EH; trade name, manufactured by Microfluidex International Corporation, using GLOZ interaction chamber) with a pressure controlled to be 1750 kg/cm² to obtain a silver behenate dispersion. During the cooling operation, a dispersion temperature of 18° C. was achieved by providing coiled heat exchangers fixed before and after the interaction chamber and controlling the temperature of the refrigerant.

<<Preparation of 25 weight % dispersion of reducing agent>>

10 kg of 1,1-bis(2-hydroxy-3,5-dimethylphenyl)-3,5,5-trimethylhexane and 10 kg of a 20 weight % aqueous solution of denatured polyvinyl alcohol (Poval MP203, manufactured by Kuraray Co. Ltd.) were added with 16 kg of water, and mixed sufficiently to form slurry. The slurry was fed by a diaphragm pump to a sand mill of horizontal type (UVM-2, manufactured by Imex Co.) containing zirconia beads having a mean diameter of 0.5 mm, and dispersed for 3 hours and 30 minutes. Then, the slurry was added with 0.2 g of benzothiazolinone sodium salt and water so that the concentration of the reducing agent could become 25% by weight to obtain a reducing agent dispersion. The reducing agent particles contained in the reducing agent dispersion obtained as described above had a median diameter of 0.42 $\mu$m and the maximum particle size of 2.0 $\mu$m or shorter. The obtained reducing agent dispersion was filtered through a polypropylene filter having a pore size of 10.0 Mm to remove dusts and so forth, and stored.

<<Preparation of 10 weight % dispersion of mercapto compound>>

5 kg of 1-phenyl-2-heptyl-5-mercapto-1,3,4-triazole and 5 kg of a 20 weight % aqueous solution of denatured polyvinyl alcohol (Poval MP203, manufactured by Kuraray Co., Ltd.) were added with 8.3 kg of water, and mixed sufficiently to form slurry. The slurry was fed by a diaphragm pump to a sand mill of horizontal type (UVM-2, manufactured by Imex Co.) containing zirconia beads having a mean diameter of 0.5 mm, and dispersed for 6 hours. Then, the slurry was added with water so that the concentration of the mercapto compound could become 10 weight % to obtain a mercapto compound dispersion. The mercapto compound particles contained in the mercapto compound dispersion obtained as described above had a median diameter of 0.40 $\mu$m and the maximum particle size of 2.0 $\mu$m or less. The obtained mercapto compound dispersion was filtered through a polypropylene filter having a pore size of 10.0 $\mu$m to remove dusts and so forth, and stored. The dispersion was filtered again through a polypropylene filter having a pore size of 10 $\mu$m immediately before use.

<<Preparation of 20 weight % dispersion of organic polyhalogenated compound 1>>

5 kg of tribromomethylnaphthylsulfone, 2.5 kg of a 20 weight % aqueous solution of denatured polyvinyl alcohol (Poval MP203, manufactured by Kuraray Co., Ltd.) and 213 g of 20 weight % aqueous solution of sodium triisopropylnaphthalenesulfonate were added with 10 kg of water, and mixed sufficiently to form slurry. The slurry was fed by a diaphragm pump to a sand mill of horizontal type (UVM-2, manufactured by Imex Co.) containing zirconia beads having a mean diameter of 0.5 mm, and dispersed for 5 hours. Then, the slurry was added with 0.2 g of benzisothiazolinone sodium salt and water so that the concentration of the organic polyhalogenated compound could become 20 weight % to obtain an organic polyhalogenated compound dispersion. The organic polyhalogenated compound particles contained in the polyhalogenated compound dispersion obtained as described above had a median diameter of 0.36 $\mu$m and the maximum particle size of 2.0 $\mu$m or less. The obtained organic polyhalogenated compound dispersion was filtered through a polypropylene filter having a pore size of 3.0 $\mu$m to remove dusts and so forth, and stored.

<<Preparation of 25 weight % dispersion of organic polyhalogenated compound 2>>

A dispersion was prepared in the same manner as the preparation of the 20 weight % dispersion of organic polyhalogenated compound 1 except that 5 kg of N-butyl-3-tribromomethanesulfonylbenzamide was used instead of 5 kg of tribromomethylnaphthylsulfone, diluted so that the concentration of the organic polyhalogenated compound could become 25 weight %, and filtered. The organic polyhalogenated compound particles contained in the organic polyhalogenated compound dispersion obtained as described above had a median diameter of 0.38 $\mu$m and the maximum particle size of 2.0 $\mu$m or less. The obtained organic polyhalogenated compound dispersion was filtered through a polypropylene filter having a pore size of 3.0 $\mu$m to remove dusts and so forth, and stored.

<<Preparation of 30 weight % dispersion of organic polyhalogenated compound 3>>

A dispersion was prepared in the same manner as the preparation of the 20 weight % dispersion of organic polyhalogenated compound 1 except that 5 kg of tribromomethylphenylsulfone was used instead of 5 kg of tribromomethylnaphthylsulfone and the amount of the 20 weight % aqueous solution of MP203 was changed to 5 kg, diluted so that the concentration of the organic polyhalogenated compound could become 30 weight %, and filtered. The organic polyhalogenated compound particles contained in the organic polyhalogenated compound dispersion obtained as described above had a median diameter of 0.41 $\mu$m and the maximum particle size of 2.0 $\mu$m or less. The obtained organic polyhalogenated compound dispersion was filtered through a polypropylene filter having a pore size of 3.0 $\mu$m to remove dusts and so forth, and stored. The dispersion was stored at 10° C. or less until use.

<<Preparation of 5 weight % solution of phthalazine compound>>

8 kg of denatured polyvinyl alcohol (Poval MP-203, manufactured by Kuraray Co., Ltd.) was dissolved in 174.57 kg of water and then added with 3.15 kg of 20 weight % aqueous solution of sodium triisopropylnaphthalenesulfonate and 14.28 kg of 70 weight % aqueous solution of 6-isopropylphthalazine to obtain a 5 weight % solution of 6-isopropylphthalazine.

<<Preparation of 20 weight % dispersion of pigment>>

64 g of C.I. Pigment Blue 60 and 6.4 g of Demor N manufactured by Kao Corporation were added with 250 g of water and mixed sufficiently to provide slurry. Then, 800 g of zirconia beads having a mean diameter of 0.5 mm were placed in a vessel together with the slurry and the slurry was dispersed by a dispersing machine (¼ G Sand Grinder Mill; manufactured by Imex Co.) for 25 hours to obtain a pigment dispersion. The pigment particles contained in the pigment dispersion obtained as described above had a mean particle size of 0.21 $\mu$m.

<<Preparation of 40 weight % SBR latex>>

SBR latex purified by ultrafiltration (UF) was obtained as follows.

The SBR latex mentioned below diluted by 10 times with distilled water was diluted and purified by using an UF-purification module FS03-FC-FUYO3A1 (manufactured by Daisen Membrane System K. K.) until the ion conductivity became 1.5 mS/cm, and added with Sandet-BL (manufactured by SANYO CHEMICAL INDUSTRIES, LTD.) to a concentration of 0.22% by weight. Further, the latex was added with NaOH and NH$_4$OH so that the ratio of Na$^+$ ion:NH$_4^+$ ion could become 1:2.3 (molar ratio) to adjust pH to 8.4. At this point, the concentration of the latex was 40% by weight.

(SBR latex: a latex of -St(68)-Bu(29)-AA(3)-, wherein the numerals in the parentheses indicate the contents in terms of % by weight, St represents styrene, Bu represents butadiene and AA represents acrylic acid)

The latex had the following characteristics: mean particle size of 0.1 μm, concentration of 45%, equilibrated moisture content of 0.6% by weight at 25° C. and relative humidity 60%, and ion conductivity of 4.2 mS/cm (measured for the latex stock solution (40%) at 25° C. by using a conductometer, CM-30S, -manufactured by Toa Electronics, Ltd.), pH 8.2.

<<Preparation of coating solution for emulsion layer (photosensitive layer)>>

1.1 g of the 20 weight % aqueous dispersion of the pigment obtained above, 103 g of an silver salt of an organic acid dispersion, 5 g of the 20 weight % aqueous solution of polyvinyl alcohol, PVA-205 (manufactured by Kuraray Co., Ltd.), 25 g of the 25 weight % dispersion of the reducing agent, 12.2 g in total of the dispersions of organic polyhalogenated compounds 1 to 3 (weight ratio=2:5:2), 6.2 g of the 10 weight % dispersion of mercapto compound, 106 g of the 40 weight % SBR latex purified by ultrafiltration (UF) and undergone pH adjustment, and 18 ml of the 5 weight % solution of the phthalazine compound were combined, added with 10 g of Silver halide mixed emulsion A, and mixed sufficiently to prepare a coating solution for emulsion layer. The coating solution for emulsion layer was fed as it was to a coating die in such a feeding amount giving a coating amount of 70 ml/m² and coated.

The viscosity of the coating solution for emulsion layer described above was measured by a B-type viscometer manufactured by Tokyo Keiki K. K. and found to be 85 [mPa•s] at 40° C. (Rotor No. 1, 60 rpm).

The viscosity of the coating solution was measured at 25° C. by an RFS fluid spectrometer produced by Rheometric Far East Co., Ltd., and found to be 1500, 220, 70, 40 and 20 [mPa•s] at shear rates of 0.1, 1, 10, 100 and 1000 [1/second], respectively.

<<Preparation of coating solution for intermediate layer on the emulsion layer surface>>

772 g of 10 weight % aqueous solution of polyvinyl alcohol, PVA-205 (manufactured by Kuraray Co., Ltd.), 5.3 g of the 20 weight % dispersion of the pigment, and 226 g of 27.5 weight % latex of methyl methacrylate/styrene/butyl acrylate/hydroxyethyl methacrylate/acrylic acid copolymer (copolymerization Pu ratio (by weight) 664/9/20/5/2) were added with 2 ml of a 5 weight % aqueous solution of Aerosol OT (manufactured by American Cyanamid Company), 10.5 ml of a 20 weight % aqueous solution of phthalic acid diammonium salt and water in such an amount giving a total amount of 880 g to form a coating solution for intermediate layer. This coating solution was fed to a coating die in such an amount that gave a coating amount of 10 ml/m².

The viscosity of the coating solution measured by a B-type viscometer at 40° C. (Rotor No. 1, 60 rpm) was 21 [mPa•s].

<<Preparation of coating solution for 1st protective layer on emulsion layer surface>>

64 g of inert gelatin was dissolved in water, added with 80 g of 27.5 weight % latex solution of methyl methacrylate/ styrene/butyl acrylate/hydroxyethyl methacrylate/acrylic acid copolymer (copolymerization ratio (by weight): 64/9/ 20/5/2), 23 ml of a 10 weight % methanol solution of phthalic acid, 23 ml of 10 weight % aqueous solution of 4-methylphthalic acid, 28 ml of 1 N sulfuric acid, 5 ml of 5 weight % aqueous solution of Aerosol OT (manufactured by American Cyanamid Company), 0.5 g of phenoxyethanol, 0.1 g of benzoisothiazolinone, and water in such an amount that gave a total amount of 750 g to form a coating solution. The coating solution was mixed with 26 ml of 4 weight % chromium alum by a static mixer immediately before coating, and fed to a coating die in such an amount that gave a coating amount of 18.6 ml/m².

The viscosity of the coating solution measured by a B-type viscometer (Rotor No. 1, 60 rpm) at 40° C. was 17 [mPa•s].

<<Preparation of coating solution for 2nd protective layer on emulsion layer surface>>

80 g of inert gelatin was dissolved in water, added with 102 g of 27.5 weight % latex solution of methyl methacrylate/styrene/butyl acrylate/hydroxyethyl methacrylate/acrylic acid copolymer (copolymerization ratio (by weight): 64/9/20/5/2), 3.2 ml of 5 weight % solution of N-perfluorooctylsulfonyl-N-propylalanine potassium salt, 32 ml of 2 weight % aqueous solution of polyethylene glycol mono(N-perfluorooctylsulfonyl-N-propyl-2-aminoethyl) ether [average polymerization degree of ethylene oxide =15], 23 ml of 5 weight % aqueous solution of Aerosol OT (manufactured by American Cyanamid Company), 4 g of polymethyl methacrylate microparticles (mean particle size: 0.7 μm), 21 g of polymethyl methacrylate microparticles (mean particle size: 6.4 μm), 1.6 g of 4-methylphthalic acid, 4.8 g of phthalic acid, 44 ml of 1 N sulfuric acid, 10 mg of benzoisothiazolinone and water in such an amount that gave a total amount of 650 g. The mixture was further mixed with 445 ml of an aqueous solution containing 4 weight % chromium alum and 0.67 weight % of phthalic acid by a static mixer immediately before coating to form a coating solution for surface protective layer, which was fed to a coating die in such an amount that gave a coating amount of 8.3 ml/m².

The viscosity of the coating solution measured by a B-type viscometer (Rotor No. 1, 60 rpm) at 40° C. was 9 [mPa•s].

<<Preparation of photothermographic material>>

On the back side of the aforementioned support having an undercoat layer, the coating solution for antihalation layer and the coating solution for back surface protective layer were simultaneously applied as stacked layers so that the applied solid content amount of the solid microparticle dye in the antihalation layer could become 0.04 g/m², and the applied amount of gelatin in the protective layer should become 1.7 g/m², and dried to form an antihalation back layer.

Then, on the side opposite to the back side, an image-forming layer (coated silver amount of the silver halide was 0.14 g/m²), intermediate layer, first protective layer, and second protective layer were simultaneously applied in this order from the undercoat layer by the slide bead application method as stacked layers to form Sample 101 of photothermographic material.

The coating was performed at a speed of 160 m/min. The gap between the tip of coating die and the support was set to be 0.14 to 0.28 mm, and the coated width was controlled so that it could spread by 0.5 mm each at both sides compared with the projecting slit width of the coating solution. The pressure in the reduced pressure chamber was adjusted to be lower than the atmospheric pressure by 392 Pa. In this case, handling, temperature and humidity were controlled so that the support could not be electrostatically charged, and electrostatic charge was further eliminated by ionized wind immediately before the coating. In the subsequent chilling zone, the material was blown with air showing a dry-bulb temperature of 18° C. and a wet-bulb temperature of 12° C. for 30 seconds to cool the coating solutions. Then, in the floating type drying zone in a coiled shape, the material was blown with drying air showing a dry-bulb temperature of 30° C. and a wet-bulb temperature of 18° C.

for 200 seconds. Subsequently, the material was passed through a drying zone of 70° C. for 20 seconds, and then another drying zone of 90° C. for 10 seconds, and cooled to 25° C. to evaporate the solvent in the coating solution. The average wind velocity of the wind applied to the coated layer surface in the chilling zone and the drying zones was 7 m/sec.

The prepared photothermographic material showed matting degrees of 550 seconds for the photosensitive layer side, and 130 seconds for the back surface, in terms of Beck's smoothness.

Samples 002 to 016 were prepared in the exactly same manner as in the preparation of Sample 001 except that the complexes according to the present invention were used in the coated amounts shown in Table 1 instead of the reducing agent, 1,1-bis(2-hydroxy-3,5-dimethylphenyl)-3,5,5-trimethylhexane, and evaluated for image storability. In Table 1, the coated amounts of the complexes of the present invention are shown as relative amounts in mole % with respect to 100 mole % of the reducing agent used in Sample 001.

<<Evaluation of image storability>>

Each of the photographic materials was light-exposed and heat-developed (about 120° C.) by using Fuji Medical Dry Laser Imager FM-DP L (provided with a semiconductor laser of 660 nm, maximum output: 60 mW (IIIB)).

Image storability was evaluated by storing the photothermographic materials after the heat development in a dark place for 1 day under a condition of 55° C. and 60% relative humidity, and measuring density change ΔDmin before and after the storage in white portions by using a densitometer. The results are shown in Table 1.

TABLE 1

| Sample No. | Complex | Relative coated amount (mol %) | Image storability ΔDmin | Note |
|---|---|---|---|---|
| 001 | — | — | 0.131 | Comparative |
| 002 | (1) | 100 | 0.038 | Invention |
| 003 | (2) | 80 | 0.033 | Invention |
| 004 | (3) | 65 | 0.041 | Invention |
| 005 | (4) | 50 | 0.047 | Invention |
| 006 | (8) | 50 | 0.037 | Invention |
| 007 | (10) | 90 | 0.032 | Invention |
| 008 | (17) | 100 | 0.020 | Invention |
| 009 | (19) | 65 | 0.029 | Invention |
| 010 | (21) | 100 | 0.021 | Invention |
| 011 | (22) | 100 | 0.022 | Invention |
| 012 | (23) | 65 | 0.016 | Invention |
| 013 | (24) | 50 | 0.053 | Invention |
| 014 | (27) | 65 | 0.051 | Invention |
| 015 | (29) | 65 | 0.047 | Invention |
| 016 | (31) | 65 | 0.049 | Invention |

As seen from the results shown in Table 1, the photothermographic materials utilizing the bisphenol-phosphorous compound complexes represented by the general formula (1) showed markedly improved image storability.

EXAMPLE 7

Preparation of thermally processed image recording material

Structures of the compounds used in Example 7 are shown below.

Compound G

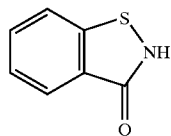

Dye A

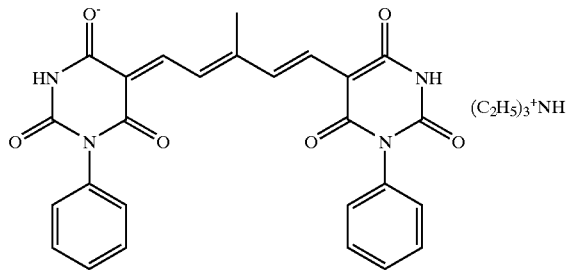

Compound A

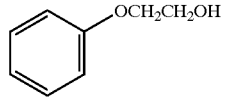

Sensitizing dye A

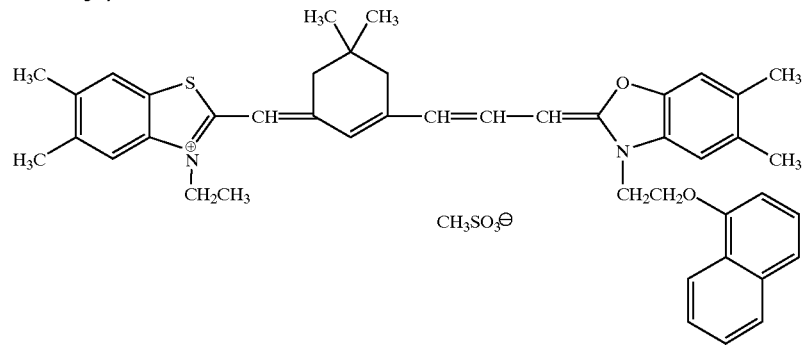

Compound B

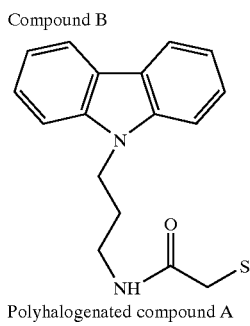

Polyhalogenated compound A

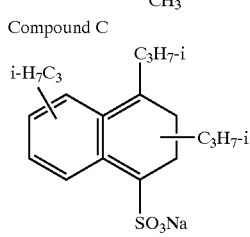

Compound C

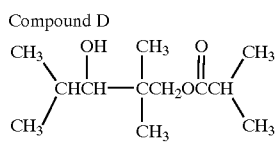

Compound D

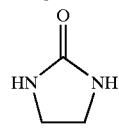

Compound S

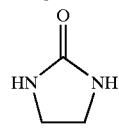

Nucleating agent 62

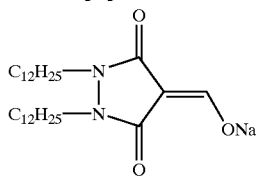

Polyhalogenated compound B

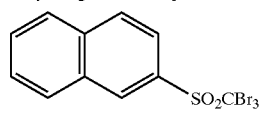

Compound Z

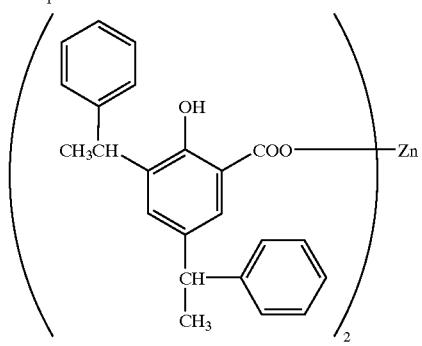

Compound E

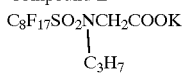

$C_8F_{17}SO_2NCH_2COOK$
         |
         $C_3H_7$

Compound F

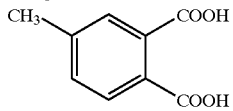

<<Preparation of PET support>>

Using terephthalic acid and ethylene glycol, PET having an intrinsic viscosity IV of 0.66 (measured in phenol/tetrachloroethane=6/4 (weight ratio) at 25° C.) was obtained in a conventional manner. The PET was pelletized, and the pellets were dried at 130° C. for 4 hours, melted at 300° C., then extruded from a T-die, and quenched to prepare an unstretched film having such a thickness that the film thickness after thermal fixation should become 120 μm.

The film was stretched along the longitudinal direction by 3.3 times using rollers having different peripheral speeds and then stretched along the transverse direction by 4.5 times using a tenter. In this case, the temperatures were 110° C. and 130° C., respectively. Thereafter, the film was subjected to thermal fixation at 240° C. for 20 seconds and relaxed by 4% along the transverse direction at the same temperature. Then, after chucks of the tenter were released, the both edges of the film were knurled, and the film was rolled up at 4.8 kg/cm² to provide a roll of PET support having a width of 2.4 m, length of 3500 m and thickness of 120 μm.

<<Coating of undercoat>>

Undercoat layer (a) and Undercoat layer (b) having the following compositions were applied successively on both sides of the PET support obtained above, and each dried at 180° C. for 4 minutes. Thickness of Undercoat layer (a) was 2.0 μm.

| (1) Composition of Undercoat layer (a) | |
|---|---|
| Polymer latex (A) (core shell type latex comprising 90 weight % of core and 10 weight % of shell, core: vinylidene chloride/methyl acrylate/methyl methacrylate/acrylonitrile/acrylic acid = 93/3/3/0.9/0.1 (weight %), shell: vinylidene chloride/methyl acrylate/methyl methacrylate/acrylonitrile/acrylic acid = 88/3/3/3/3 (weight %), weight average molecular weight; 38000) | 3.0 g/m² as solid content |
| 2,4-Dichloro-6-hydroxy-S-triazine | 23 mg/m² |
| Matting agent (polystyrene, mean diameter; 2.4 μm) | 1.5 mg/m² |

-continued

| (2) Composition of Undercoat layer (b) | |
|---|---|
| Deionized gelatin ($Ca^{2+}$ content; 0.6 ppm, jelly strength; 230 g) | 50 mg/m$^2$ |

<<Formation of back layer>>

The following electroconductive layer and protective layer were successively applied to one side of the PET support provided with the two undercoat layers obtained above, and each dried at 180° C. for 4 minutes to prepare a back layer.

| (1) Composition of electroconductive layer | |
|---|---|
| Julimer ET-410 (Nihon Junyaku Co., Ltd.) | 96 mg/m$^2$ |
| Alkali-treated gelatin (molecular weight; about 10000, $Ca^{2+}$ content; 30 ppm) | 42 mg/m$^2$ |
| Deionized gelatin ($Ca^{2+}$ content; 0.6 ppm) | 8 mg/m$^2$ |
| Compound G | 0.2 mg/m$^2$ |
| Polyoxyethylene phenyl ether | 10 mg/m$^2$ |
| Sumitex Resin M-3 (water-soluble melamine resin, Sumitomo Chemical Co., Ltd.) | 18 mg/m$^2$ |
| Dye A | Amount giving optical density of 1.2 at 783 nm |
| SnO$_2$/Sb (weight ratio: 9/1, acicular grains, short axis/long axis = 20–30, Ishihara Sangyo Kaisha, Ltd.) | 160 mg/m$^2$ |
| Matting agent (Polymethyl methacrylate, mean particle size: 5 µm) | 7 mg/m$^2$ |
| (2) Composition of protective layer | |
| Polymer latex (B) (copolymer of methyl methacrylate/styrene/2-ethylhexyl acrylate/ 2-hydroxyethylethyl methacrylate/acrylic acid = 59/9/26/5/1 (weight %)) | 1000 mg/m$^2$ as solid content |
| Polystyrenesulfonate (molecular weight: 1000–5000) | 2.6 mg/m$^2$ |
| Cellosol 524 (Chukyo Yushi Co., Ltd.) | 25 mg/m$^2$ |
| Sumitex Resin M-3 (water-soluble melamine compound, Sumitomo Chemical Co., Ltd.) | 218 mg/m$^2$ |

<<Heat treatment during transportation>>

(1) Heat treatment

The PET support with back layers and undercoat layers prepared as described above was subjected to heat treatment by introducing it into a heat treatment zone having a total length of 200 m set at 160° C., and transporting it at a tension of 3 kg/cm$^2$ and a transportation speed of 20 m/minute.

(2) Post-heat treatment

Following the aforementioned heat treatment, the support was passed through a zone at 40° C. for 15 seconds, and rolled up. The rolling up tension for this operation was 10 kg/cm$^2$.

<<Preparation of coating solution for image-forming layer>>

(1) Preparation of organic acid silver salt dispersion 87.6 g of Behenic acid (product name: Edenor C22-85R, Henkel Corp.), 423 ml of distilled water, 49.2 ml of 5 N NaOH aqueous solution and 120 ml of tert-butyl alcohol were mixed and allowed to react at 75° C. for 1 hour with stirring to prepare a sodium behenate solution. Separately, 206.2 ml of an aqueous solution containing of 40.4 g of silver nitrate was prepared and maintained at 10° C. A reaction vessel containing 635 ml of distilled water and 30 ml of tert-butyl alcohol were maintained at 30° C., and added with the whole volumes of the sodium behenate solution and the aqueous silver nitrate solution at constant flow rates over 62 minutes and 10 seconds, and 60 minutes, respectively. This operation was performed in such a manner that only the aqueous silver nitrate solution should be added for 7 minutes and 20 seconds after starting the addition of the aqueous silver nitrate solution. Then, addition of the sodium behenate solution was started so that only the sodium behenate solution could be added for 9 minutes and 30 seconds after the completion of the addition of the aqueous silver nitrate solution. During this procedure, the internal temperature of the reaction vessel was maintained at 30° C., and controlled so that the mixture temperature could not be raised. Piping of the sodium behenate solution addition system was warmed by a steam tracing, and steam amount was controlled so that the solution temperature at the outlet of addition nozzle tip could be 75° C. Further, piping of the aqueous silver nitrate solution addition system was maintained by circulating cooled water outside the double pipe. The addition points of the sodium behenate solution and the aqueous silver nitrate solution were symmetrically located with respect to a stirring axis, and the heights thereof were controlled so as not to contact with the reaction mixture.

After the completion of the addition of the sodium behenate solution, the mixture was left at that temperature for 20 minutes with stirring so that the temperature of the mixture was lowered to 25° C. Thereafter, the solid content was separated by suction filtration, and washed with water until the conductivity of the filtrate became 30 µS/cm. The solid content obtained as described above was stored as a wet cake without being dried.

The shape of the obtained silver behenate grains was analyzed by electron microphotography. The obtained grains were scaly crystals having an average projected area diameter of 0.52 µm, a mean grain thickness of 0.14 µm, and a variation coefficient of 15% for mean diameter as spheres.

To the wet cake corresponding to 100 g of dry solid content, 7.4 g of polyvinyl alcohol (trade name: PVA-217, average polymerization degree: about 1700) and water were added to make the total amount 385 g, and the resulting mixture was preliminarily dispersed in a homomixer. Then, the preliminarily dispersed stock solution was treated three times in a dispersing machine (trade name: Microfluidizer M-110S-EH, manufactured by Microfluidex International Corporation, using G10Z interaction chamber) under a pressure controlled to be 1,750 kg/cm$^2$ to obtain a silver behenate dispersion as organic acid silver salt dispersion. During the cooling operation, a desired dispersion temperature was established by providing coiled heat exchangers fixed before and after the interaction chamber and controlling the temperature of the refrigerant.

The silver behenate grains contained in the silver behenate dispersion obtained as described above were grains having a volume weighted mean diameter of 0.52 µm, and a variation coefficient of 15%. The grain size was measured by Master Sizer X manufactured by Malvern Instruments Ltd. Further, when the grains were evaluated by electron microphotography, they were grains having a ratio of long axis length and short axis length of 1.5, a grain thickness of 0.14 µm, and a mean aspect ratio (ratio of diameter of projected area of grains as spheres and grain thickness) of 5.1.

(2) Preparation of photosensitive silver halide emulsion

In 700 ml of water, 11 g of alkali-treated gelatin (calcium content: 2700 ppm or less), 30 mg of potassium bromide and 10 mg of sodium benzenethiosulfonate were dissolved. After the solution was adjusted to pH 5.0 at a temperature of 40° C., 159 ml of an aqueous solution containing 18.6 g of silver nitrate and an aqueous solution containing 1 mol/l of potassium bromide, $5\times10^{-6}$ mol/l of $(NH_4)_2RhCl_5(H_2O)$ and $2\times10^{-5}$ mol/l of $K_3IrCl_6$ were added by the control double jet method over 6 minutes and 30 seconds while pAg was maintained at 7.7. Then, 476 ml of an aqueous solution containing 55.5 g of silver nitrate and an aqueous solution containing 1 mol/l of potassium bromide and $2\times10^{-5}$ mol/l of $K_3IrCl_6$ were added by the control double jet method over 28 minutes and 30 seconds while pAg was maintained at 7.7.

Then, the pH was lowered to cause coagulation precipitation to effect desalting, 0.17 g of Compound A and 51.1 g of low molecular weight gelatin having an average molecular weight of 15,000 (calcium content: 20 ppm or less) were added, and pH and pAg were adjusted to 5.9 and 8.0, respectively. The grains obtained were cubic grains having a mean grain size of 0.08 μm, a variation coefficient of 9% for projected area and a [100] face ratio of 90%.

The temperature of the photosensitive silver halide grains obtained as described above was raised to 60° C., and added with 76 μmol per mole of silver of sodium benzenethiosulfonate. After 3 minutes, 71 μmol of triethylthiourea was further added, the grains were ripened for 100 minutes, then added with $5\times10^{-4}$ mol/l of 4-hydroxy-6-methyl-1,3,3a,7-tetrazaindene, and cooled to 40° C. Then, Sensitizing Dye A and Compound B were added in amounts of $12.8\times10^{-4}$ mol and $6.4\times10^{-3}$ mol per mole of the photosensitive silver halide with stirring while the emulsion was maintained at 40° C. After 20 minutes, the emulsion was quenched to 30° C. to complete the preparation of photosensitive silver halide emulsion.

(3) Preparation of solid microparticle dispersion of ultrahigh contrast agent

An ultrahigh contrast agent (Nucleating agent A, 10 g) was added with 2.5 g of polyvinyl alcohol (PVA-217, produced by Kuraray Co., Ltd.) and 87.5 g of water, and the mixture was thoroughly stirred to form slurry. The slurry was left for 3 hours. Then, 240 g of 0.5-mm zirconia beads were prepared and put together with the slurry into a vessel. The contents in the vessel were dispersed in a dispersing machine (¼ G Sand Grinder Mill, manufactured by Imex Co.) for 10 hours to prepare a solid microparticle dispersion of the ultrahigh contrast agent. In this dispersion, 80 weight % of the microparticles had a particle size of from 0.1 to 1.0 μm, and the mean particle size was 0.5 μm.

(4) Preparation of solid microparticle dispersion of reducing agent

To 25 g of 1,1-bis(2-hydroxy-3,5-dimethylphenyl)-3,5,5-trimethylhexane, 25 g of 20 weight % aqueous solution of MP Polymer (MP-203, produced by Kuraray Co., Ltd.), 0.1 g of Safinol 104E (Nisshin Kagaku Co., Ltd.), 2 g of methanol and 48 ml of water were added, and the mixture was thoroughly stirred to form slurry. The resulting slurry was left for 3 hours. Then, 360 g of 1-mm zirconia beads were put together with the slurry into a vessel. The contents in the vessel were dispersed in a dispersing machine (¼ G Sand Grinder Mill, manufactured by Imex Co.) for 3 hours to prepare a solid microparticle dispersion of the reducing agent. In this dispersion, 80 weight % of the microparticles had a particle size of from 0.3 to 1.0 μm.

(5) Preparation of solid microparticle dispersion of polyhalogenated compound 30 g of Polyhalogenated compound A was added with 4 g of MP Polymer (MP-203, produced by Kuraray Co., Ltd.), 0.25 g of Compound C and 66 g of water, and the mixture was thoroughly stirred to form slurry. Then, 200 g of 0.5-mm zirconia silicate beads were put together with the slurry into a vessel. The contents in the vessel were dispersed in a dispersing machine (1/16 G Sand Grinder Mill, manufactured by Imex Co.) for 5 hours to prepare a dispersion of Polyhalogenated compound A. In this dispersion, 80 weight % of the microparticles had a particle size of from 0.3 to 1.0 μm.

A solid microparticle dispersion of Polyhalogenated compound B was also prepared in the same manner as that for Polyhalogenated compound A. The microparticles in this dispersion had a similar particle size.

(6) Preparation of solid microparticle dispersion of zinc compound 30 g of Compound Z was added with 3 g of MP Polymer (MP-203, produced by Kuraray Co., Ltd.) and 87 ml of water, and the mixture was thoroughly stirred to form slurry. The slurry was left for 3 hours. Then, the slurry was treated in the same manner as the preparation of the solid microparticle dispersion of reducing agent mentioned in the above (4) to prepare a solid microparticle dispersion of zinc compound (Compound Z). In this dispersion, 80 weight % of the microparticles had a particle size of from 0.3 to 1.0 μm.

(7) Preparation of coating solution for image-forming layer

The following components were added to the dispersion of silver salt of an organic acid (silver behenate) prepared in the above (1) in the specified amounts per 1 mole of silver in the dispersion, and added with water to prepare a coating solution for image-forming layer.

| | |
|---|---|
| Photosensitive silver halide emulsion obtained in the above (2) | 0.05 mole as Ag |
| Solid microparticle dispersion of nucleating agent obtained in the above (3) | 17.1 g as solid |
| Solid microparticle dispersion of reducing agent obtained in the above (4) | 166 g as solid |
| Polyhalogenated compound dispersion A obtained in the above (5) | 0.06 mole as solid |
| Polyhalogenated compound dispersion B obtained in the above (5) | 0.02 mole as solid |
| Solid microparticle dispersion of zinc compound obtained in the above (6) | 10.5 g as solid |
| Binder: LACSTAR 3307B (SBR latex, produced by Dai-Nippon Ink & Chemicals, Inc., glass transition temperature: 17° C.) | 470 g as solid |
| Sodium ethanethiosulfonate | 2.2 mmole |
| 5-Methylbenzotriazole | 1.36 g |
| Polyvinyl alcohol (PVA-235, Kuraray Co., Ltd.) | 12.1 g |
| 6-Isopropylphthalazine | 16.5 g |
| Sodium dihydrogenorthophosphate dihydrate | 0.37 g |
| Dye A | Amount giving optical density of 0.3 at 783 nm (about 0.50 g) |

<<Preparation of coating solution for protective layers on image-forming side>>

(1) Preparation of coating solution for protective layer (a) on image-forming side 965 g of a polymer latex solution containing copolymer of methyl methacrylate/styrene/2-ethylhexyl acrylate/2-hydroxyethyl methacrylate/acrylic acid =58.9/8.6/25.4/5.1/2

(weight %) (glass transition temperature: 57° C., solid content: 21.5 weight %, average particle diameter: 120 nm, containing Compound D as a film-forming aid in an amount of 15 weight % relative to solid content of the latex was added with water, 1.62 g of Compound E, 3.15 g of Compound S, 1.98 g of matting agent (polystyrene particles, mean diameter: 7 μm, variation coefficient of 8% for mean particle diameter) and 23.6 g of polyvinyl alcohol (PVA-235, Kuraray Co., Ltd.) and further added with water to form a coating solution for protective layer (a) on image-forming side.

(2) Preparation of coating solution for protective layer (b) on image-forming side 630 g of a polymer latex solution containing copolymer of methyl methacrylate/styrene/2-ethylhexyl acrylate/2-hydroxyethyl methacrylate/acrylic acid =58.9/8.6/25.4/5.1/2 (weight %) (glass transition temperature: 54° C., solid content: 21.5 weight %, average particle diameter: 70 nm, containing Compound D as a film-forming aid in an amount of 15 weight % relative to solid content of the latex) was added with water, 6.30 g of 30 weight % solution of carnauba wax (Cellosol 524, Chukyo Yushi Co., Ltd.), 0.72 g of Compound E, 7.95 g of Compound F, 0.90 g of Compound S. 1.18 g of matting agent (polystyrene particles, average diameter: 7 μm) and 8.30 g of polyvinyl alcohol (PVA-235, Kuraray Co., Ltd.) and further added with water to form a coating solution for protective layer (b) on image-forming side.

<<Preparation of thermally processed image recording material>>

On the side opposite to the side provided with the back layer of the aforementioned PET support subjected to the heat treatment during transportation, i.e., the side of the support coated with Undercoat layer (a) and Undercoat layer (b), the coating solution for image-forming layer was coated so that the coated silver amount could become 1.6 g/m². Further, the coating solution for Protective layer (a) for image-forming surface was coated on the image-forming layer simultaneously with the coating solution for image-forming layer as laminated layers, so that the coated solid content of the polymer latex could become 1.31 g/m². Then, the coating solution for Protective layer (b) for image-forming surface was coated on the coated layer, so that the coated solid content of the polymer latex could become 3.02 g/m² to prepare a thermally processed image recording material. The film surface pH of the obtained thermally processed image recording material on the image-forming side was 4.9, and the Beck's smoothness was 660 seconds. As for the opposite surface, the film surface pH was 5.9 and the Beck's smoothness was 560 seconds.

A sample was prepared by using a complex of the general formula (1) in such a coated amount that a developed density substantially comparable to the aforementioned samples instead of 1,1-bis(2-hydroxy-3,5-dimethylphenyl)-3,5,5-trimethylhexane, and evaluated for image storability.

<<Evaluation>>

(1) Light exposure

Each thermally processed image recording material was light exposed for $2\times10^{-8}$ seconds by using a laser light-exposure apparatus of single channel cylindrical inner surface type provided with a semiconductor laser with a beam diameter (½ of FWHM of beam intensity) of 12.56 μm, laser output of 50 mW and output wavelength of 783 nm. The exposure time was adjusted by controlling the mirror revolution number, and exposure was adjusted by changing output. The overlap coefficient of the light exposure was 0.449.

(2) Heat development

Figure 2:
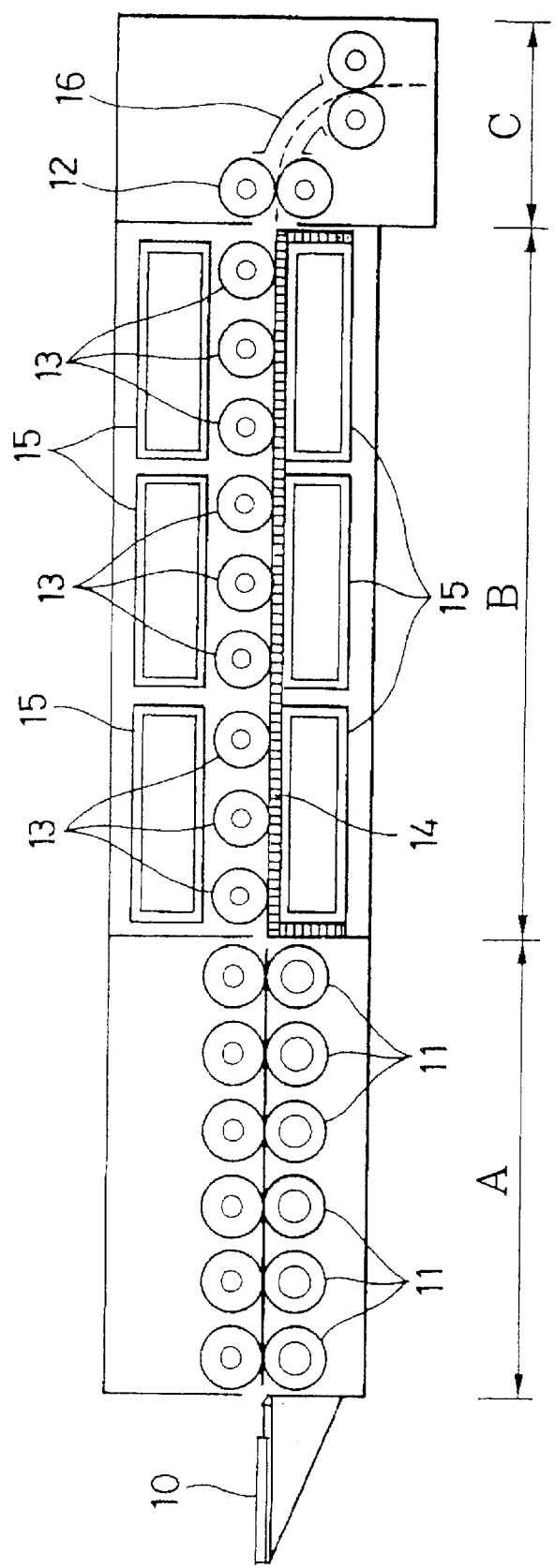
FIG. 2 shows an exemplary heat developing apparatus that can be used for the thermally processed image recording material of the present invention. In the figure, there are shown a thermally processed image recording material 10, carrying-in roller pairs 11, carrying-out roller pairs 12, rollers 13, a flat surface 14, heaters 15, and guide panels 16. The apparatus consists of a preheating section A, a heat development section B, and a gradual cooling section C.

The light-exposed thermally processed image recording material obtained in the above (1) was heat-developed by using a heat-developing apparatus as shown in FIG. 2. The apparatus shown in FIG. 2 comprises carrying-in roller pairs 11 (upper rollers are silicone rubber rollers, and lower rollers are aluminum heating rollers), which carry a thermally processed image recording material 10 into the heating section while making the material in a flat shape and preheating it, and carrying-out roller pairs 12, which carry out the thermally processed image recording material 10 after heat development from the heating section while maintaining the material to be in a flat shape. The thermally processed image recording material 10 is heat-developed while it is conveyed by the carrying-in roller pairs 11 and then by the carrying-out roller pairs 12. Conveying means for carrying the thermally processed image recording material 10 under the heat development is provided with multiple rollers 13 so that they could be contacted with the side of the image-forming layer, and a flat surface 14 adhered with Teflon non-woven fabric is provided on the opposite side so that it should be contacted with the back surface. The heat development was performed at a linear transportation speed of 20 mm/second. The thermally processed image recording material 10 is conveyed by driving of the multiple rollers 13 contacted with the image-forming layer side, while the back surface slides on the flat surface 14. Heaters 15 are provided over the rollers 13 and under the flat surface 14 so that the thermally processed image recording material 10 could be heated from the both sides. As the heating means, panel heaters are used in this case. While clearance between the rollers 13 and the flat surface 14 may vary depending on the material of the flat surface, it is suitably adjusted to a clearance that allows the conveyance of the thermally processed image recording material 10. The temperature precision as for the transverse direction was ±1° C.

The heating section is constituted by a preheating section A comprising the carrying-in roller pairs 11 and a heat development section B comprising the heaters 15. The heat development was performed in the preheating section A existing upstream from the heat development section B at 90–110° C. for 15 seconds, and in the heat development section at 120° C. for 20 seconds. The temperature distribution of the preheating section and the heat development section was ±0.5° C. or less. Driving units of the preheating section and the heat development section were independent from each other, and speed difference as to the heat development section was adjusted to −0.5% to −1%.

Moreover, guide panels 16 are provided downstream from the heat development section B, and they constitute a gradual cooling section C together with the carrying-out roller pairs 12.

The guide panels 16 are preferably composed of a material of low heat conductivity. The cooling was performed for 15 seconds so as not to cause deformation of the thermally processed image recording material 10.

(3) Evaluation of image storability in the dark after heat development

The thermally processed image recording material subjected to the light exposure and development was evaluated in the same manner as in Example 6.

As a result, when a complex of the present invention was used, the material showed superior performance similar to that observed in Example 6. Thus, it was revealed that superior image storability could be obtained even in an ultrahigh contrast thermally processed image recording material.

What is claimed is:

1. A thermally processed image recording material comprising a non-photosensitive silver salt of an organic acid, a reducing agent for silver ions and a binder on one surface of a support, wherein the thermally processed image recording material comprises at least one bisphenol-phosphorus compound complex represented by the following general formula (1):

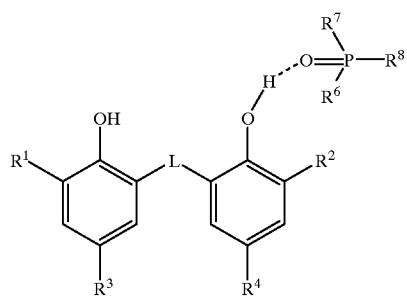

wherein $R^1$, $R^2$, $R^3$ and $R^4$ each independently represent hydrogen atom or a group that can be a substituent on a benzene ring; L represents —S— group or a —$CHR^5$— group where $R^5$ represents hydrogen atom or an alkyl group; $R^6$, $R^7$ and $R^8$ each independently represent an alkyl group, an aryl group, a heterocyclic group, —$N(R^9)(R^{10})$ or —$O(R^9)$ where $R^9$ and $R^{10}$ each independently represent an alkyl group, an aryl group or a heterocyclic group; and two or more groups selected from $R^6$, $R^7$, $R^8$, $R^9$ and $R^{10}$ may be bound together to form a ring.

2. The thermally processed image recording material according to claim 1, which contains at least one photosensitive silver halide.

3. The thermally processed image recording material according to claim 1, wherein the amount of bisphenol-phosphorus compound complex is 5–50 mole % per mole of silver on the side having the image-forming layer.

4. The thermally processed image recording material according to claim 3, wherein the amount of bisphenol-phosphorus compound complex is 10–40 mole % per mole of silver on the side having the image-forming layer.

5. The thermally processed image recording material according to claim 1, wherein the bisphenol-phosphorus compound complex is selected from the group consisting of:

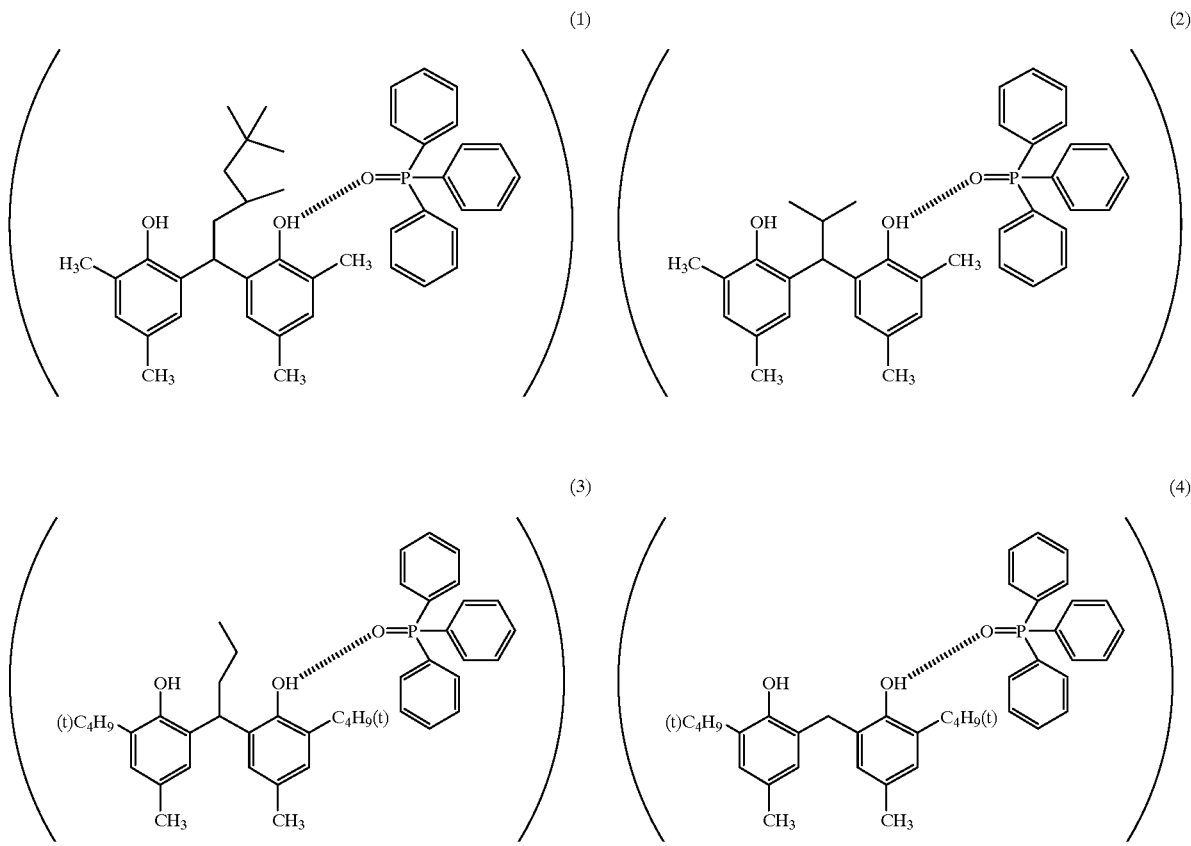

-continued
(5)
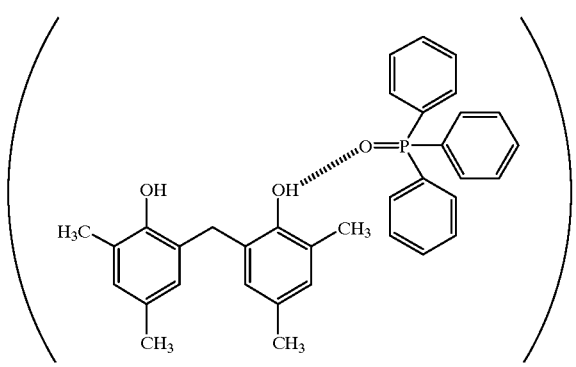
(6)
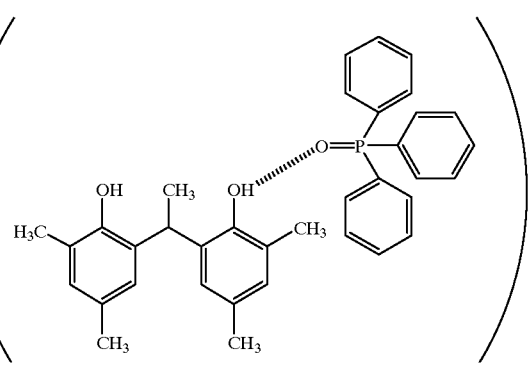
(7)
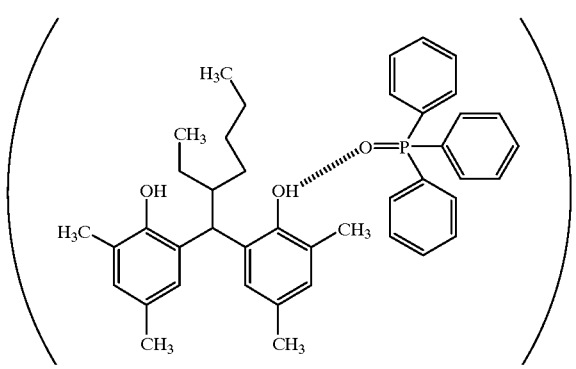
(8)
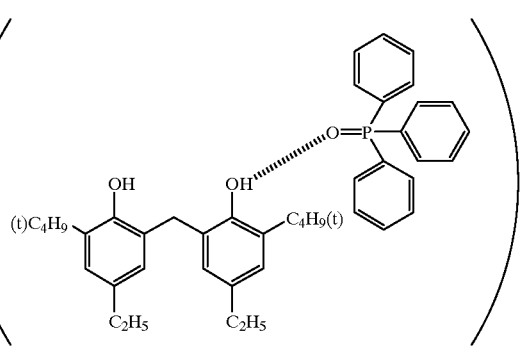
(9)
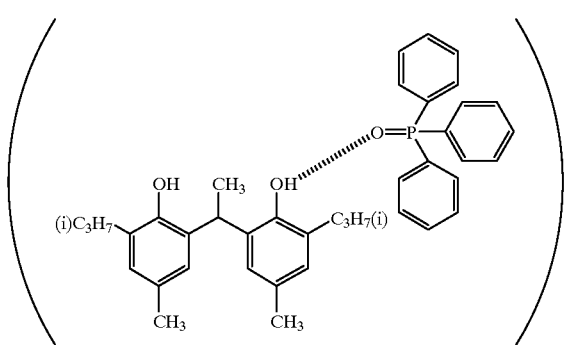
(10)
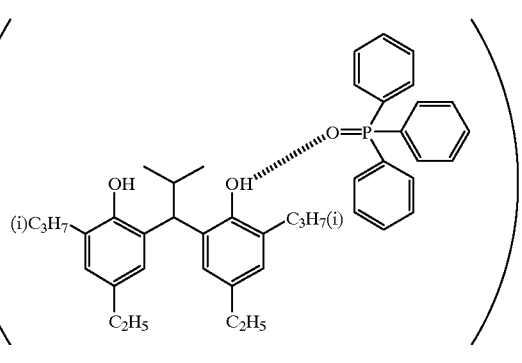
(11)
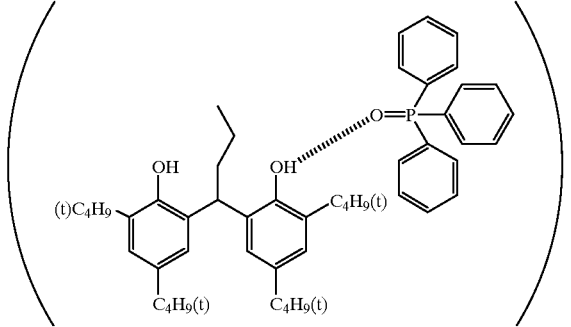
(12)
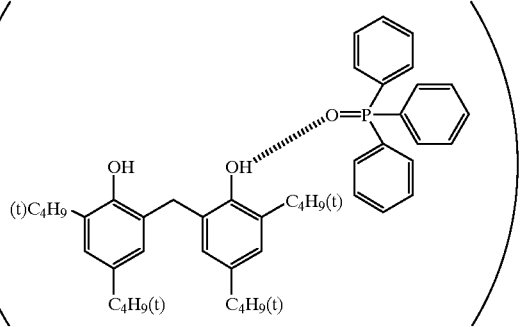

-continued
(13)
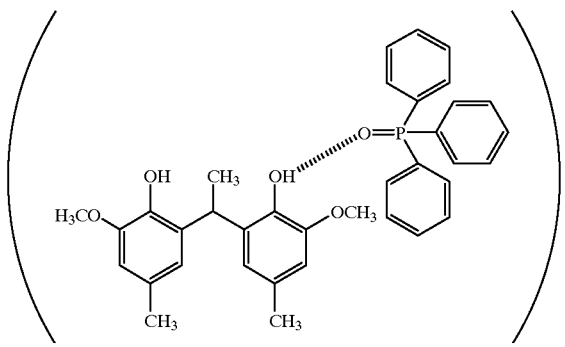
(14)
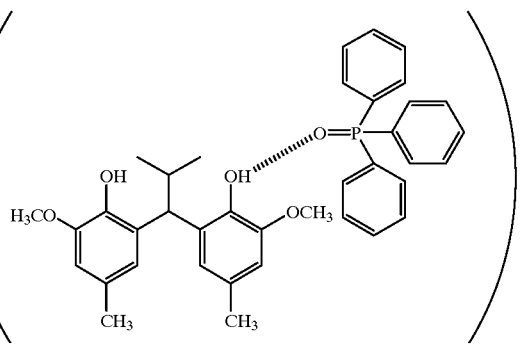
(15)
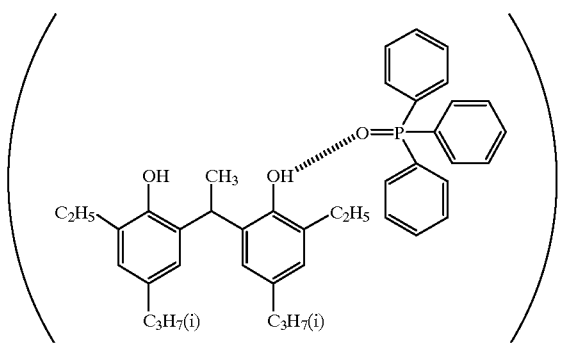
(16)
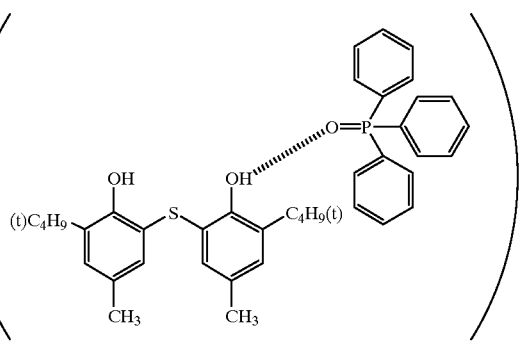
(17)
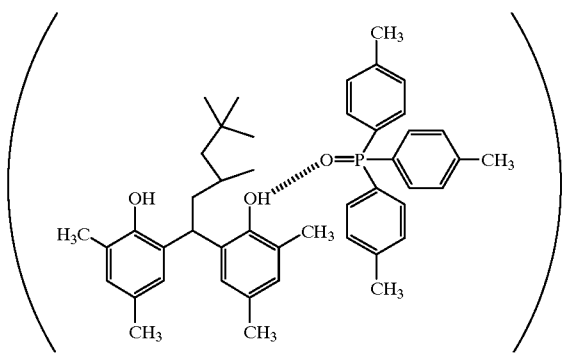
(18)
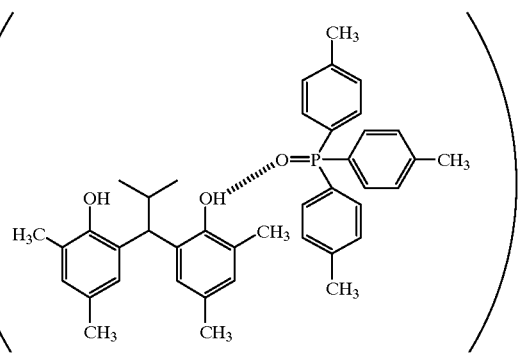
(19)
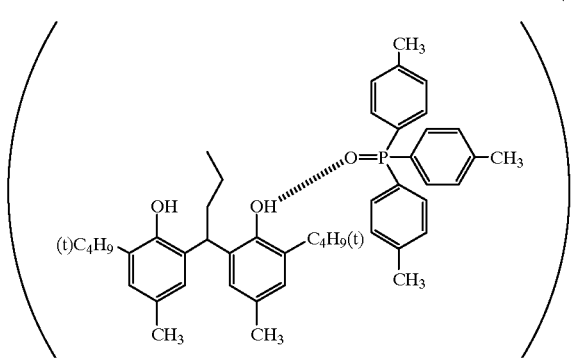
(20)
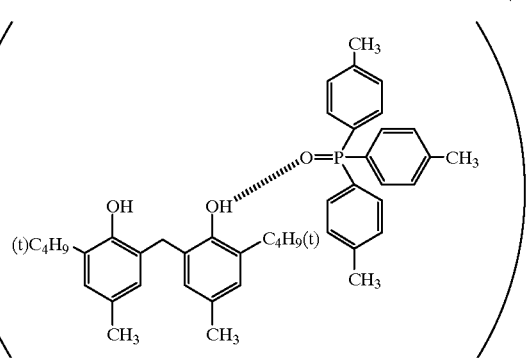

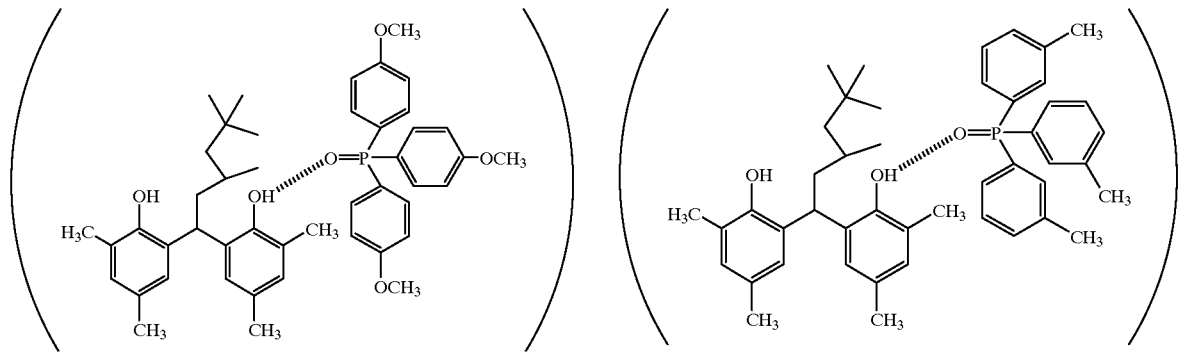
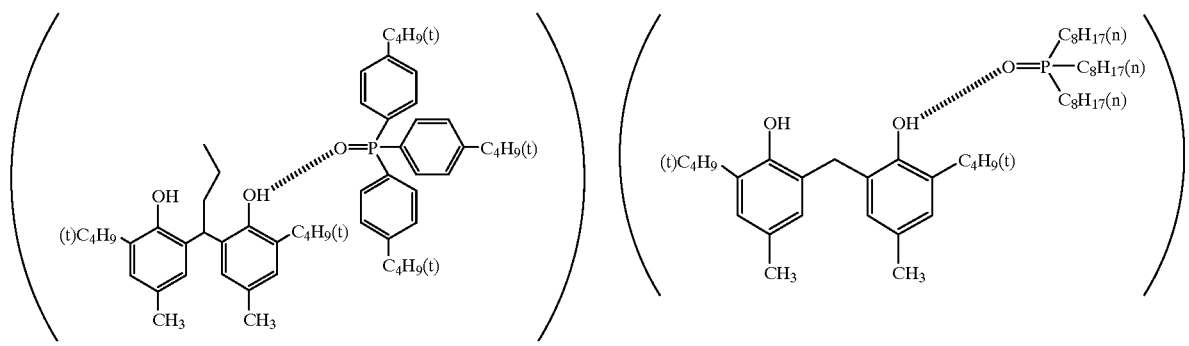
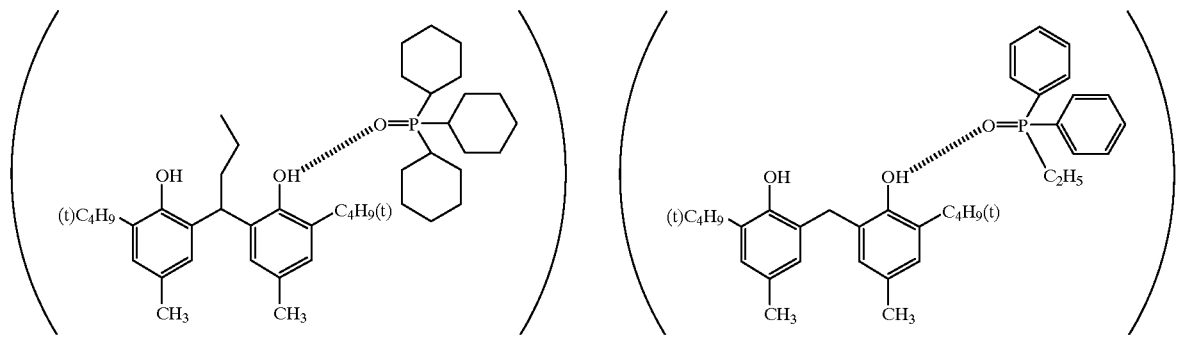
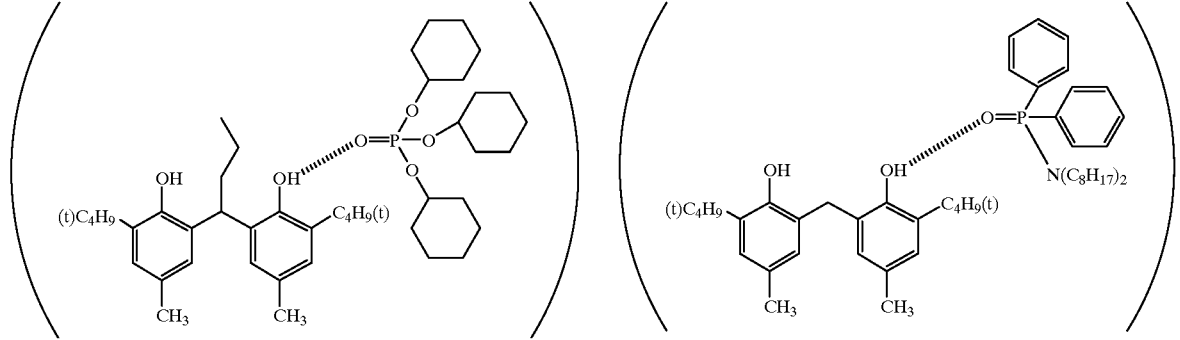

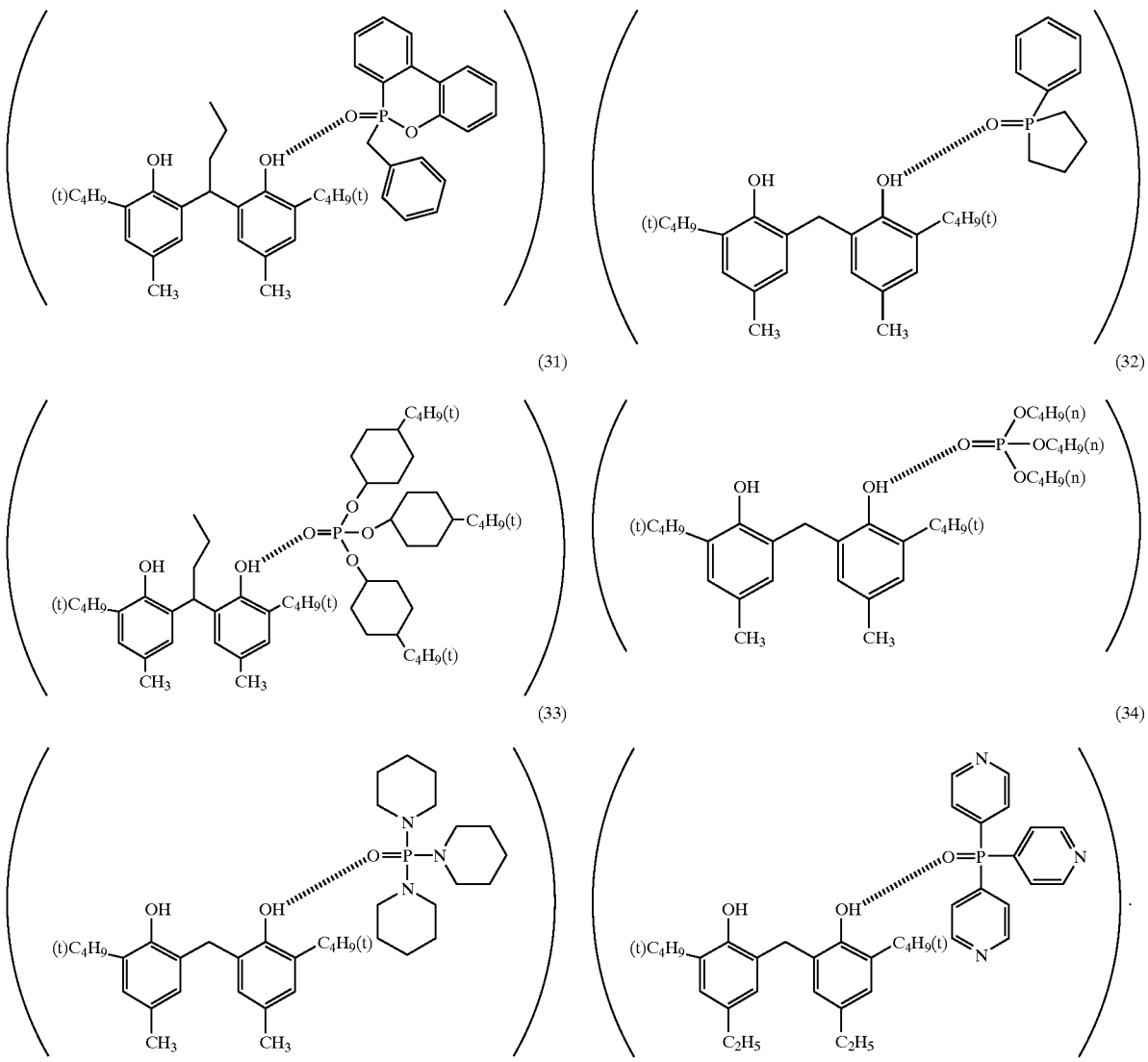

6. The thermally processed image recording material according to claim 2, wherein the photosensitive silver halide is present in an amount of 0.03 to 0.6 g/m$^2$.

7. The thermally processed image recording material according to claim 1, wherein the photosensitive silver halide comprises an iridium compound selected from the group consisting of hexachloroiridium, hexammineiridium, trioxalatoiridium and hexacyanoiridium.

* * * * *